(12) United States Patent
Giardina et al.

(10) Patent No.: US 6,277,862 B1
(45) Date of Patent: *Aug. 21, 2001

(54) QUINOLINE DERIVATIVES

(75) Inventors: Giuseppe Arnaldo Maria Giardina, Milan; Mario Grugni, Verbania; Luca Francesco Raveglia; Carlo Farina, both of Milan, all of (IT)

(73) Assignee: SmithKline Beecham S.p.A., Milan (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/077,151
(22) PCT Filed: Nov. 22, 1996
(86) PCT No.: PCT/EP96/05203
 § 371 Date: May 22, 1998
 § 102(e) Date: May 22, 1998
(87) PCT Pub. No.: WO97/21680
 PCT Pub. Date: Jun. 19, 1997

(30) Foreign Application Priority Data

Nov. 24, 1995 (IT) ................................. MI95A2461
Aug. 2, 1996 (IT) ................................. MI96A1689

(51) Int. Cl.[7] ........................ A61K 31/47; C07D 215/38; C07D 215/60
(52) U.S. Cl. ................... 514/311; 514/312; 514/313; 514/314; 546/153; 546/159; 546/169
(58) Field of Search .................... 514/311–314; 546/169, 153, 159

(56) References Cited

FOREIGN PATENT DOCUMENTS

9602509 * 2/1996 (WO).

OTHER PUBLICATIONS

Chemical Abstracts 124:232269, 1995.*
CA 130:148135, 1998.*
CA 130:125092, 1998.*
CA 127:248121, 1997.*
CA 127:95200, 1997.*

* cited by examiner

Primary Examiner—D. Margaret Seaman
(74) Attorney, Agent, or Firm—Nora Stein-Fernandez; Stephen Venetianer; Charles M. Kinzig

(57) ABSTRACT

A compound, or a solvate or a salt thereof, of formula (I), wherein, Ar is an optionally substituted aryl or a $C_{5-7}$ cycloalkdienyl group, or an optionally substituted single or fused ring aromatic heterocyclic group; R, $R_1$, $R_2$ and $R_3$ are as defined in the description; a process for the preparation of such a compound, a pharmaceutical composition containing such a compound or composition in medicine.

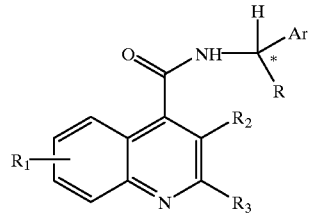

(I)

29 Claims, No Drawings

QUINOLINE DERIVATIVES

The present invention relates to novel compounds, in particular to novel quinoline derivatives, to processes for the preparation of such compounds, to pharmaceutical compositions containing such compounds and to the use of such compounds in medicine.

The mammalian peptide Neurokinin B (NKB) belongs to the Tachykinin (TK) peptide family which also include Substance P (SP) and Neurokinin A (NKA). Pharmacological and molecular biological evidence has shown the existence of three subtypes of TK receptor ($NK_1$, $NK_2$ and $NK_3$) and NKB binds preferentially to the $NK_3$ receptor although it also recognises the other two receptors with lower affinity (Maggi et al, 1993, *Auton. Pharmacol.,* 13, 23–93).

Selective peptidic $NK_3$ receptor antagonists are known (Drapeau, 1990 *Regul. Pept.,* 31, 125–135), and findings with peptidic $NK_3$ receptor agonists suggest that NKB, by activating the $NK_3$ receptor, has a key role in the modulation of neural input in airways, skin, spinal cord and nigrostriatal pathways (Myers and Undem, 1993, *J. Physiol.,* 470, 665–679; Counture et al., 1993, *Regul. Peptides,* 46, 426–429; Mccarson and Krause, 1994, *J. Neurosci.,* 14 (2), 712–720; Arenas et al. 1991, *J. Neurosci.,* 11, 2332–8). However, the peptide-like nature of the known antagonists makes them likely to be too labile from a metabolic point of view to serve as practical therapeutic agents.

We have now discovered a novel class of non-peptide NK-3 antagonists which are far more stable from a metabolic point of view than the known peptidic NK-3 receptor antagonists and are of potential therapeutic utility. These compounds also have NK-2 antagonist activity and are therefore considered to be of potential use in the prevention and treatment of a wide variety of clinical conditions which are characterized by overstimulation of the tachykinin receptors, in particular NK-3 and NK-2.

These conditions include respiratory diseases, such as chronic obstructive pulmonary disease (COPD), asthma, airway hyperreactivity, cough; inflammatory diseases such a inflammatory bowel disease, psoriasis, fibrositis, osteoarthritis, rheumatoid arthritis and inflammatory pain; neurogenic inflammation or peripheral neuropathy, allergies such as eczema and rhinitis; opthalmic diseases such as ocular inflammation, conjunctivitis, vernal conjuctivitis and the like; cutaneous diseases, skin disorders and itch, such as cutaneous wheal and flare, contact dermatitis, atopic dermatitis, urticaria and other eczematoid dermatitis; adverse immunological reactions such as rejection of transplanted tissues and disorders related to immune enhancement or suppression such as systhemic lupus erythematosis; gastrointestinal (GI) disorders and diseases of the GI tract such as disorders associated with the neuronal control of viscera such as ulcerative colitis, Crohn's disease and urinary incontinence; renal disorders and disorders of the bladder function, (hereinafter referred to as the 'Primary Conditions').

In addition, certain of the present compounds are indicated to be particularly selective for the periphery rather than the central nervous system. These compounds are therefore considered to be especially useful in the treatment of those components of the 'Primary Conditions' which require a peripheral-selectivity.

Certain compounds of this invention also show CNS activity and hence are considered to be of particular use in the treatment of disorders of the central nervous system such as anxiety, depression, psychosis and schizophrenia; neurodegenerative disorders such as AIDS related dementia, senile dementia of the Alzheimer type, Alzheimer's disease, Down's syndrome, Huntington's disease, Parkinson's disease, movement disorders and convulsive disorders (for example epilepsy); demyelinating diseases such as multiple sclerosis and amyotrophic lateral sclerosis and other neuropathological disorders such as diabetic neuropathy, AIDS related neuropathy, chemotherapy-induced neuropathy and neuralgia; addiction disorders such as alcoholism; stress related somatic disorders; reflex sympathetic dystrophy such as shoulder/hand syndrome; dysthymic disorders; eating disorders (such as food intake disease); fibrosing and collagen diseases such as scleroderma and eosinophilic fascioliasis; disorders of the blood flow caused by vasodilation and vasospastic diseases such as angina, migraine and Reynaud's disease and pain or nociception, for example, that is attributable to or associated with any of the foregoing conditions especially the transmission of pain in migraine, (hereinafter referred to as the 'Secondary Conditions').

Certain of these compounds are selective antagonists of the NK-3 receptor relative to the NK-2 receptor.

In an alternative aspect, certain of these compounds are combined NK-2/NK-3 antagonists and hence are considered to be particularly suitable for the treatment and/or prophylaxis of respiratory diseases, such as chronic obstructive pulmonary disease (COPD), asthma, airway hyperreactivity and cough.

The compounds are also considered to be useful as diagnostic tools for assessing the degree to which neurokinin-3 receptor activity (normal, overactivity or underactivity) is implicated in a patient's symptoms.

According to the present invention there is provided a compound of formula (I):

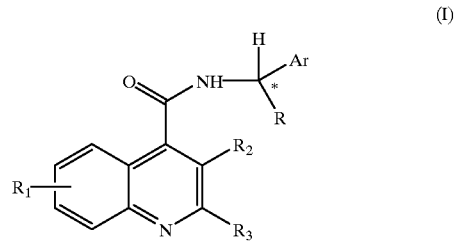

(I)

or a solvate thereof, or a salt thereof, wherein, Ar is an optionally substituted aryl or a $C_{5-7}$ cycloalkdienyl group, or an optionally substituted single or fused ring aromatic heterocyclic group;

R is $C_{1-6}$ alkyl, $C_{3-7}$ cycloalkyl, $C_{3-7}$ cycloalkylalkyl, optionally substituted phenyl or phenyl $C_{1-6}$ alkyl, an optionally substituted five-membered heteroaromatic ring comprising up to four heteroatoms selected from O and N, hydroxy $C_{1-6}$ alkyl, amino $C_{1-6}$ alkyl, $C_{1-6}$ alkylaminoalkyl, di $C_{1-6}$ alkylaminoalkyl, $C_{1-6}$ acylaminoalkyl, $C_{1-6}$ alkoxyalkyl, $C_{1-6}$ alkylcarbonyl, carboxy, $C_{1-6}$ alkoxyxcarbonyl, $C_{1-6}$ alkoxycarbonyl $C_{1-6}$ alkyl, aminocarbonyl, $C_{1-6}$ alkylaminocarbonyl, di $C_{1-6}$ alkylaminocarbonyl, halogeno $C_{1-6}$ alkyl; or R is a group —$(CH_2)_p$- wherein p is 2 or 3 which group forms a ring with a carbon atom of Ar;

$R_1$ represents hydrogen or up to four optional subtitutents selected from the list consisting of: $C_{1-6}$ alkyl, $C_{1-6}$ alkenyl, aryl, $C_{1-6}$ alkoxy, hydroxy, halogen, nitro, cyano, carboxy, carboxamido, sulphonamido, $C_{1-6}$ alkoxycarbonyl, trifluoromethyl, acyloxy, phthalimido, amino or mono- and di-$C_{1-6}$ alkylamino;

$R_2$ represents a moiety —O—$(CH_2)_n$-X wherein X is alkyl optionally substituted with one or two groups selected from hydroxy and amino; carboxy, cyano, $C_{1-6}$ alkoxycarbonyl, aminocarbonyl, mono- or di-$C_{1-6}$ alkylaminocarbonyl, amino-$C_{1-6}$-alkylaminocarbonyl or mono- or di-$C_{1-6}$-alkylamino-$C_{1-6}$-alkylaminocarbonyl; or X is a group —$NX_1X_2$ wherein $X_1$ and $X_2$ each independently represent hydrogen, alkylcarbonyl, arylcarbonyl, heteroarylcarbonyl, aryl-$C_{1-6}$-alkylcarbonyl, heteroaryl $C_{1-6}$-alkylcarbonyl, aminocarbonyl, mono- or bis-$C_{1-6}$ alkylaminocarbonyl, amino $C_{1-6}$ alkylcarbonyl, mono-or bis-$C_{1-6}$ alkylamino $C_{1-6}$ alkylcarbonyl, a moiety of formula —CO—T—CO—$T_1$ or a 5 to 9 membered single or fused ring cycloalkyl group optionally comprising 1 or 2 nitrogen atoms and optionally 1 or 2 additional heteroatoms selected from O or N and wherein one or two ring atoms are optionally substituted with $C_{1-6}$ alkyl, said ring being optionally fused to a benzene ring; wherein the above mentioned aryl and heteroaryl groups are optionally substituted with up to two groups selected from: hydroxy, $C_{1-6}$ alkoxy, hydroxy-$C_{1-6}$ alkyl, amino-$C_{1-6}$-alkyl, mono- or bis-$C_{1-6}$-alkylamino, mono- or bis-$C_{1-6}$-alkylamino-$C_{1-6}$-alkyl, amino-$C_{1-6}$-alkoxy, mono- or bis-$C_{1-6}$-alkylamino-$C_{1-6}$-alkoxy, carboxy, C-$_{1-6}$-alkylcarbonyl, C-$_{1-6}$-alkoxycarbonyl, carboxy-$C_{1-6}$ alkyl, carboxy-$C_{1-6}$ alkoxy and C-$_{1-6}$-alkylcarbonyl $C_{1-6}$ alkoxy; and wherein the alkyl moiety of any heteroaryl-$C_{1-6}$-alkyl or aryl-$C_{1-6}$-alkyl group is optionally substituted with an amino, a mono-$C_{1-6}$-alkylamino or a bis-$C_{1-6}$-alky amino group; or X is a C-linked single or fused ring heterocyclic group, any ring being saturated or unsaturated and consisting of 5- to 6-ring atoms, said ring atoms comprising 1 or 2 nitrogen atoms and optionally 1 or 2 additional heteroatoms selected from O or N and wherein one or two ring atoms are optionally substituted with $C_{1-6}$ alkyl, hydroxy, amino, mono- or bis-$C_{1-6}$-alkylamino or an oxo substituent; and n is zero or an integer in the range of from 1 to 7 providing that when X is a group —$NX_1X_2$, n is only an integer in the range of from 2 to 7 and providing that $X_1$ and $X_2$ are not simultaneously hydrogen; or $R_2$ represents a moiety-NH—CO—NHY wherein Y represents $C_{1-6}$-alkyl, aryl, aryl $C_{1-3}$-alkyl, a moiety —$(CH_2)_p$-$X_3$ wherein p is an integer in the range of from 1 to 4 and $X_3$ is carboxy, $C_{1-6}$ alkoxycarbonyl, or a moiety —CO—NH—$(CH_2)_q$-$NX_4X_5$ wherein q is an integer in the range of from 2 to 4 and $X_4$ and $X_5$ each independently represent hydrogen, $C_{1-6}$ alkyl or $C_{1-6}$ alkylcarbonyl;

$R_3$ is branched or linear $C_{1-6}$ alkyl, $C_{3-7}$ cycloalkyl, $C_{4-7}$ cycloalkylalkyl, optionally substituted aryl, or an optionally substituted single or fused ring aromatic heterocyclic group,; T is a $C_{1-6}$ alkylene or $C_{2-6}$ alkenylene group; and $T_1$ is hydroxy or $C_{1-6}$ alkoxy.

Suitably, Ar represents phenyl

Suitably, R represents $C_{1-6}$ alkyl, for example ethyl.

Preferably, R is ethyl.

Preferably, $R_1$ represents hydrogen.

When $R_2$ represents a moiety —O—$(CH_2)_n$-X wherein n is an integer in the range of from 1 to 7, such as 1, 2 and 3, suitable values of X include carboxy, $C_{1-6}$ alkoxycarbonyl, aminocarbonyl, mono- or di-$C_{1-6}$ alkylaminocarbonyl or X is a C-linked single or fused ring heterocyclic group as defined n relation to formula (I); preferably X is carboxy, $C_{1-6}$ alkoxycarbonyl, for example ethoxycarbonyl, or the said C-linked single or fused ring heterocyclic group, for example pyridyl; preferably n is 1 or 3.

In one preferred aspect $R_2$ is a group —O—$(CH_2)_n$-X wherein X represents carboxy or $C_{1-6}$ alkoxycarbonyl.

In one preferred aspect $R_2$ is a group —O—$(CH_2)_n$-X wherein X represents a C-linked single or fused ring heterocyclic group as defined in relation to formula (I).

When $R_2$ represents a moiety —O—$(CH_2)_n$-X wherein n is an integer in the range of from 2 to 7, such as 2 and 3, suitable values of X include a group —$NX_1X_2$ wherein $X_1$ and $X_2$ each independently represent hydrogen, alkylcarbonyl, heteroarylcarbonyl, arylcarbonyl, aminocarbonyl, mono- or di-$C_{1-6}$ alkylaminocarbonyl, a moiety of the above defined formula —CO—T—CO—$T_1$ or a 5- or 6-membered cycloalkyl group said group being optionally fused to a benzene ring, providing that $X_1$ and $X_2$ are not simultaneously hydrogen; preferably one of $X_1$ and $X_2$ is hydrogen and the other is selected from heteroarylcarbonyl, arylcarbonyl or a moiety of the above defined formula —CO—T—CO—$T_1$.

Examples of X include carboxy, cyano, ethoxycarbonyl, aminocarbonyl, dimethylaminocarbonyl, (2-indanyl)amino and benzoylamino.

One particular value of $R_2$ is —O—$(CH_2)_n$-X wherein n is an integer 1, 2 or 3 and X is carboxy.

One particular value of $R_2$ is —O—$(CH_2)_n$-X wherein n is an integer 1, 2 or 3 and X is ethoxycarbonyl. One particular value of $R_2$ is —O—$(CH_2)_n$-X wherein n is an integer 1, 2 or 3 and X is pyridyl.

One particular value of $R_2$ is —O—$(CH_2)_n$-X wherein n is an integer 2 or 3 and X is a group —$NX_1X_2$ wherein $X_1$ is hydrogen and $X_2$ is a 5 to 9 membered single ring cycloalkyl group ring fused to a benzene ring, for example a 2-indanylamino group, or an N-methyl-8-azabicyclo [3.2.1]oct-3-yl group One particular value of $R_2$ is —O—$(CH_2)_n$-X wherein n is an integer 2 or 3 and X is a group —$NX_1X_2$ wherein $X_1$ is hydrogen and $X_2$ is amino-$C_{1-6}$ alkylcarbonyl or mono-or bis-$C_{1-6}$ alkylamino $C_{1-6}$ alkylcarbonyl, for example 2-aminoacetyl.

One particular value of $R_2$ is —O—$(CH_2)_n$-X wherein n is an integer 2 or 3 and X is a group —$NX_1X_2$ wherein $X_1$ is hydrogen and $X_2$ is a moiety of formula —CO—T—CO $T_1$ wherein T is a $C_{1-6}$ alkylene, for example —$CH_2CH_2$— and $T_1$ is hydroxy or $C_{1-6}$ alkoxy, especially hydroxy.

One particular value of $R_2$ is —O—$(CH_2)_n$-X wherein n is an integer 2 or 3 and X is a group —$NX_1X_2$ wherein $X_1$ is hydrogen and $X_2$ is optionally substituted heteroarylcarbonyl, such as 2-pyrazinylcarbonyl and 3-amino-2-pyrazinylcarbonyl, One particular value of $R_2$ is —O—$(CH_2)_n$-X wherein n is an integer 2 or 3 and X is a group —$NX_1X_2$ wherein $X_1$ is hydrogen and $X_2$ is optionally substituted aryl-$C_{1-6}$-alkylcarbonyl group, such as 2-(methylaminomethyl) benzylcarbonyl, 2-(pyrrolidinomethyl)benzylcarbonyl, 2-(pyrrolidinoethoxy)benzylcarbonyl and (2-carboxy) benzylcarbonyl.

One preferred value of $R_2$ is —O—$(CH_2)_n$-X wherein n is an integer 2 or 3 and X is a group —$NX_1X_2$ wherein $X_1$ is hydrogen and $X_2$ is a moiety of the above defined formula —CO—T—CO—$T_1$, for example wherein T is ethylene and $T_1$ is OH.

One preferred value of $R_2$ is —O—$(CH_2)_n$-X wherein n is an integer 2 or 3 and X is a group —$NX_1X_2$ wherein $X_1$ is hydrogen and $X_2$ is and substituted aryl-$C_{1-6}$-alkylcarbonyl, for examlpe (2-carboxy)benzylcarbonyl and (2-pyrrolidinomethyl)benzylcarbonyl.

One preferred value of $R_2$ is —O—$(CH_2)_n$-X wherein n is an integer 2 or 3 and X is a group —$NX_1X_2$ wherein $X_1$ is hydrogen and $X_2$ is heteroarylcarbonyl, for example 2-pyrazinylcarbonyl.

When $R_2$ represents a moiety —O—$(CH_2)_n$-X wherein n is zero, suitable values of X include carboxy, $C_{1-6}$ alkoxycarbonyl, for example ethoxycarbonyl.

Y suitably represents aryl, for example phenyl, or a moiety —(CH$_2$)$_p$-X$_3$.

When Y is —(CH$_2$)$_p$-X$_3$, p is favourably an integer 1.

When Y is —(CH$_2$)$_p$-X$_3$, X$_3$ is suitably C$_{1-6}$ alkoxycarbonyl, for example ethoxycarbonyl.

Preferred compounds of formula (I) are those wherein:

Ar is phenyl, R is ethyl, R$_1$ is hydrogen and R$_2$ is a moiety —O—(CH$_2$)$_n$-X wherein either:

n is 1, 2 or 3 and X is carboxy, C$_{1-6}$ alkoxycarbonyl, for example ethoxycarbonyl, or the C-linked single or fused ring heterocyclic group defined in relation to formula (I), for example pyridyl; or n is 2 or 3 and X is a group —NX$_1$X$_2$ wherein X$_1$ is hydrogen and X$_2$ is moiety of the above defined formula —CO—T—CO—T$_1$, for example wherein T is ethylene and T$_1$ is OH, or X$_2$ is substituted aryl-C$_{1-6}$-alkylcarbonyl, for example (2-carboxy)benzylcarbonyl and (2-pyrrolidinomethyl)benzylcarbonyl or heteroarylcarbonyl, for example 2-pyrazinylcarbonyl.

In particular should be mentioned the compounds of examples 2, 11, 14, 29, 34, 36, 38, 39 and 40, especially 2, 11 and 40.

It should also be stated that compounds 2 and 11, especially, 14 and 29 and particularly active at the periphery and hence are considered to be especially selective for those 'Primary Conditions' which require peripheral selectivity, as discussed above.

Compounds 34, 36 and 38 are particularly selective for the NK-3 receptor relative to the NK-2 receptor.

As stated above certain of the compounds of formula (I) are combined NK-2/NK-3 antagonists and are considered to be particularly suitable for the treatment and/or prophylaxis of respiratory diseases, such as chronic obstructive pulmonary disease (COPD), asthma, airway hyperreactivity and cough. Accordingly the present invention also comprises a combined NK-2/NK-3 antagonist, especially for use in the treatment and/or prophylaxis of respiratory diseases. Also within the present invention is a method for the treatment and/or prophylaxis of respiratory diseases in mammals, such as humans, which method comprises the administration of an effective, non-toxic, pharmaceutically acceptable amount of a combined NK-2/NK-3 antagonist.

A suitable, combined NK-2/NK-3 antagonist is an antagonist having an NK-2/NK-3 binding affinity ratio in the range of from 0.05 to 20, favourably 0.1 to 10, preferably 1 to 7 and most preferably 1 to 5; thus preferred compounds are considered to be substantially equipotent antagonists of the NK-2 and NK-3 receptors.

Compounds 39 and 40 are particularly suitable as combined NK-2/NK-3 antagonists and hence are particularly suitable for the treatment and/or prophylaxis of respiratory diseases, such as chronic obstructive pulmonary disease (COPD), asthma, airway hyperreactivity and cough.

The compounds of formula (I) may have at least one asymmetric centre—for example the carbon atom labelled with an asterisk (*) in the compound of formula (I)—and therefore may exist in more than one stereoisomeric form. The invention extends to all such stereoisomeric forms and to mixtures thereof, including racemates. In particular, the invention includes compounds wherein the asterisked carbon atom in formula (I) has the stereochemistry shown in formula (Ia):

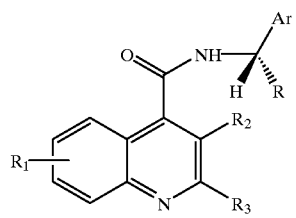

(Ia)

wherein Ar, R, R$_1$, R$_2$ and R$_3$ are as defined in relation to formula (I).

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels.

A substantially pure form will generally contain at least 50% (excluding normal pharmaceutical additives), preferably 75%, more preferably 90% and still more preferably 95% of the compound of formula (I) or its salt or solvate.

One preferred pharmaceutically acceptable form is the crystalline form, including such form in pharmaceutical composition. In the case of salts and solvates the additional ionic and solvent moieties must also be non-toxic.

Suitable salts are pharmaceutically acceptable salts.

Suitable pharmaceutically acceptable salts include the acid addition salts with the conventional pharmaceutical acids, for example maleic, hydrochloric, hydrobromic, phosphoric, acetic, fumaric, salicylic, citric, lactic, mandelic, tartaric, succinic, benzoic, ascorbic and methanesulphonic.

Suitable pharmaceutically acceptable salts include salts of acidic moieties of the compounds of formula (I) when they are present, for example salts of carboxy groups or phenolic hydroxy groups.

Suitable salts of acidic moieties include metal salts, such as for example aluminium, alkali metal salts such as lithium, sodium or potassium, alkaline earth metal salts such as calcium or magnesium and ammonium or substituted ammonium salts, for example those with lower alkylamines such as triethylamine, hydroxy alkylamines such as 2-hydroxyethylamine, bis-(2-hydroxyethyl)-amine or tri-(2-hydroxyethyl)-amine, cycloalkylamines such as bicyclohexylamine, or with procaine, dibenzylpiperidine, N-benzyl-β-phenethylamine, dehydroabietylamine, N,N'-bisdehydroabietylamine, glucamine, N-methylglucamine or bases of the pyridine type such as pyridine, collidine, quinine or quinoline.

Suitable solvates are pharmaceutically acceptable solvates.

Suitable pharmaceutically acceptable solvates include hydrates.

The term 'alkyl' when used alone or when forming part of other groups (such as the 'alkoxy' group) includes straight- or branched-chain alkyl groups containing 1 to 12 carbon atoms, suitably 1 to 6 carbon atoms, examples include methyl, ethyl, n-propyl, isopropyl, n-butyl, isobutyl or tert-butyl group.

The term 'cycloalkyl' includes groups having 3 to 12, suitably 4 to 6 ring carbon atoms.

The term 'aryl' includes phenyl and naphthyl, preferably phenyl which unless specified to the contrary optionally comprise up to five, preferably up to three substituents selected from halogen, alkyl, phenyl, alkoxy, haloalkyl, hydroxyalkyl, hydroxy, amino, nitro, cyano, carboxy, alkoxycarbonyl, alkoxycarbonylalkyl, alkylcarbonyloxy, or alkylcarbonyl groups.

The term 'aromatic heterocyclic group' or 'heteroaryl' includes groups comprising aromatic heterocyclic rings containing from 5 to 12 ring atoms, suitably 5 or 6, and comprising up to four hetero-atoms in the or each ring selected from S, O or N. Unless specified to the contrary suitable substituents for any heterocyclic group includes up to 4 substituents selected from the group consisting of: alkyl, alkoxy, aryl and halogen or any two substituents on adjacent carbon atoms, together with the carbon atoms to which they are attached, may for an aryl group, preferably a benzene ring, and wherein the carbon atoms of the aryl group represented by the said two substituents may themselves be substituted or unsustituted unsubstitut When used herein the term "halogen" refers to fluorine, chlorine, bromine and iodine, preferably fluorine or chlorine.

When used herein the term "acyl" includes residues of acids, in particular a residue of a carboxylic acid such as an alkyl- or aryl-carbonyl group.

The invention also provides a process for the preparation of a compound of formula (I), or a salt thereof and/or a solvate thereof, which process comprises reacting a compound of formula (III):

wherein R' and Ar' are R and Ar as defined for formula (I) or a group or atom convertible to R and Ar respectively, with a compound of formula (II) or an active derivative thereof:

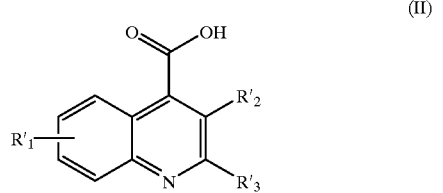

wherein R'$_1$, R'$_2$ and R'$_3$ are R$_1$, R$_2$ and R$_3$ respectively as defined in relation to formula (I) or a group convertible to R$_1$, R$_2$ and R$_3$ to form a compound of formula (Ib):

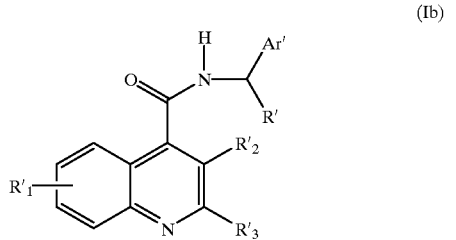

wherein Ar', R', R'$_1$, R'$_2$ and R'$_3$ are as defined above, and optionally thereafter carrying out one or more of the following optional steps:

(i) converting any one of Ar', R', R'$_1$, R'$_2$ and R'$_3$ to Ar, R, R$_1$, R$_2$ or R$_3$ respectively as required, to obtain a compound of formula (I);

(ii) converting a compound of formula (I) into another compound of formula (I); and (iii) preparing a salt of the compound of formula (I) and/or a solvate thereof.

Suitable groups convertible into other groups include protected forms of said groups.

Suitably Ar', R', R'$_1$ or R'$_3$ each represents Ar, R, R$_1$, R$_3$ respectively or a protected form thereof.

Suitably R'$_2$ represents a group other than a protected form which is convertible into R$_2$ by conventional procedures.

It is favoured if the compound of formula (II) is present as an active derivative.

A suitable active derivative of a compound of formula (II) is a transient activated form of the compound of formula (II) or a derivative wherein the carboxy group of the compound formula (II) has has been replaced by a different group or atom, for example by a carboxy halide, preferably a chloride, or an azide or a carboxylic acid anhydride.

Other suitable active derivatives include: a mixed anhydride formed between the carboxyl moiety of the compound of formula (II) and an alkyl chloroformate; an activated ester, such as a cyanomethyl ester, thiophenyl ester, p-nitrophenyl ester, p-nitrothiophenyl ester, 2,4,6-trichlorophenyl ester, pentachlorophenyl ester, pentafluorophenyl ester, N-hydroxy-phtalimido ester, N-hydroxypiperidine ester, N-hydroxysuccinimide ester, N-hydroxy benzotriazole ester; alternatively, the carboxy group of the compound of formula (II) may be activated using a carbodiimide or N,N'-carbonyldiimidazole.

The reaction between the compound of formula (II) or the active derivative thereof and the compound of formula (III) is carried out under the appropriate conventional conditions for the particular compounds chosen. Generally, when the compound of formula (II) is present as an active derivative the reaction is carried out using the same solvent and conditions as used to prepare the active derivative, preferably the active derivative is prepared in situ prior to forming the compound of formula (Ib) and thereafter the compound of formula (I) or a salt thereof and/or a solvate thereof is prepared.

For example the reaction between an active derivative of the compound of formula (II) and the compound of formula (III) may be carried out:

(a) by first preparing an acid chloride and then coupling said chloride with the compound of formula (III) in the presence of an inorganic or organic base in a suitable aprotic solvent such as dimethylformamide (DMF) at a temperature in a range from –70 to 50° C. (preferably in range from –10 to 20° C.); or (b) by treating the compound of formula (II) with a compound of formula (III) in the presence of a suitable condensing agent, such as for example N,N'-carbonyl diimidazole (CDI) or a carbodiimide such as dicyclohexylcarbodiimide (DCC) or N-dimethylaminopropyl-N'-ethylcarbodiimide, preferably in the presence of N-hydroxybenzotriazole (HOBT) to maximise yields and avoid racemization processes (see *Synthesis*, 453, 1972), in an aprotic solvent, such as a mixture of acetonitrile (MeCN) and tetrahydrofuran (THF), for example a mixture in a volume ratio of from 1:9 to 7:3 (MeCN:THF), at a temperature in the range of from –70 to 50° C. (preferably in a range of from –10 to 25° C.).

A preferred reaction is set out in Scheme 1 shown below:

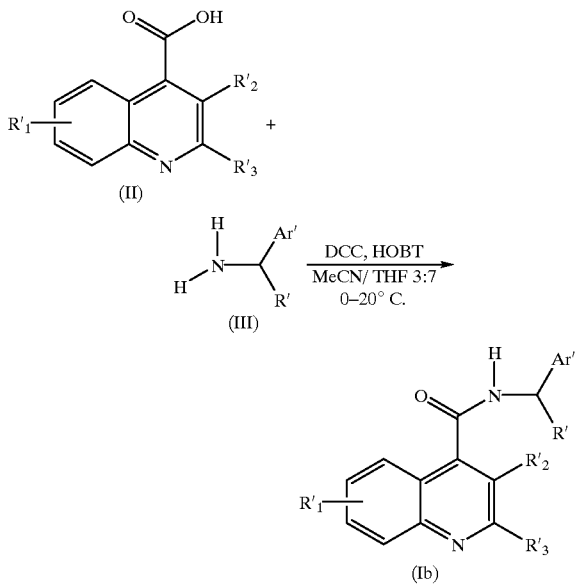

wherein Ar', R', R'$_1$, R'$_2$ and R'$_3$ are as defined above.

It will be appreciated that a compound of formula (Ib) may be converted to a compound of formula (I), or one compound of formula (I) may be converted to another compound of formula (I) by interconversion of suitable substituents. Thus, certain compounds of formula (I) and (Ib) are useful intermediates in forming other compounds of the present invention.

Accordingly, in a further aspect the invention provides a process for preparing a compound of formula (I), or a salt thereof and/or a solvate thereof, which process comprises converting a compound of the above defined formula (Ib) wherein at least one of Ar', R', R'$_1$ R'$_2$ or R'$_3$ is not Ar, R, R$_1$, R$_2$ or R$_3$ respectively, thereby to provide a compound of formula (I); and thereafter, as required, carrying out one or more of the following optional steps:

(i) converting a compound of formula (I) into another compound of formula (I); and (ii) preparing a salt of the compound of formula (I) and/or a solvate thereof.

Suitably, in the compound of formula (Ib) the variables Ar', R', R'$_1$ and R'$_3$ are Ar, R, R$_1$ or R$_3$ respectively or they are protected forms thereof and R'$_2$ is a group or atom which may be converted into a variable R$_2$ by one or more steps.

Favourably, R'$_2$ represents OH or NH$_2$.

The conversion of any group Ar', R', R'$_1$ or R'$_3$ into Ar, R, R$_1$ or R$_3$, which as stated above are usually protected forms of Ar, R, R$_1$ or R$_3$, may be carried out using appropriate conventional conditions such as the appropriate deprotection procedure.

The conversion of any group R'$_2$ into R$_2$ may be carried out using appropriate conventional reagents and conditions:

For example, when R'$_2$ is OH, the compound of formula (Ib) can be converted to compounds of formula (I) as described in Scheme 2.

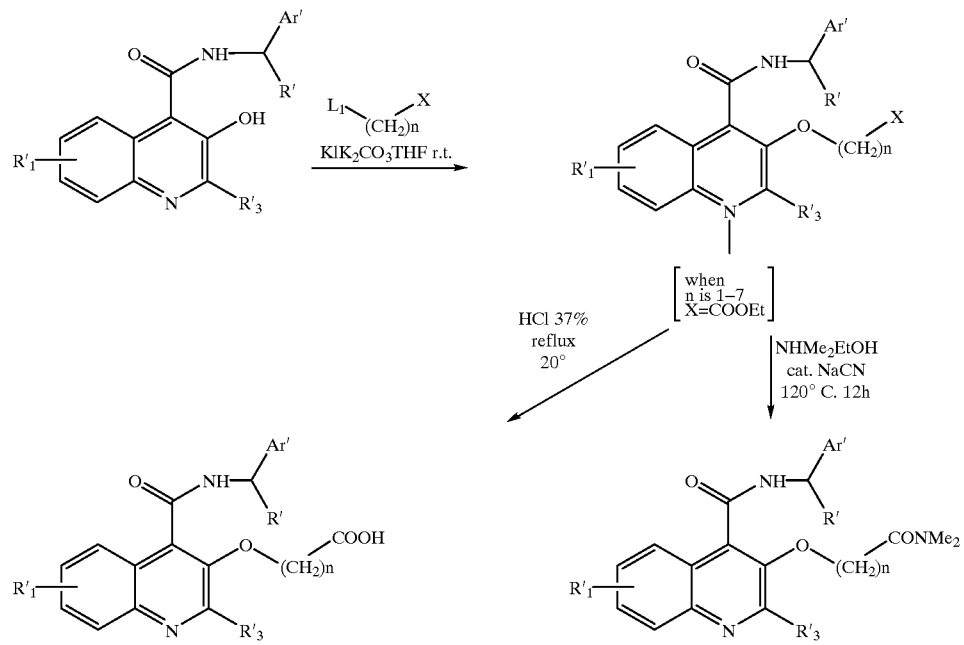

wherein Ar', R', R'$_1$, R'$_2$, R'$_3$ and X are as defined above in relation to formula (I), n is as defined in relation to formula (I) or as particularly specified in the Scheme 2 and L$_1$ is a leaving group or atom, such as a halogen atom for example a chlorine or bromine atom.

In Scheme 2, an example of X is COOEt.

In particular, when $R'_2$ is OH, it can be alkylated with an alkyl haloformate or with an ω-haloalkyl ester or ω-haloalkyl nitrile; for example, when it is alkylated with ethylbromoacetate and $K_2CO_3$ in THF, the 3-ethoxycarbonylmethoxy derivative is obtained. The resulting ester moiety can be subsequently hydrolized by refluxing in concentrated HCl, or transamidated with ammonia, a primary or a secondary amine in ethanol as solvent, at a temperature ranging from 20° to 120° C., optionally in the presence of a catalytic amount of NaCN (*J. Org. Chem,* 1987, 52, 2033).

In Scheme 3, $R'_2$=OH is converted to an ω-aminoalkoxy group by rection with ω-bromoalkylphthalimide and $K_2CO_3$ in boiling THF to obtain the phthalimidoalkoxy derivative, which is, in turn, hydrolized with hydrazine hydrate.

The amino function of the resulting ω-aminoalkoxy substituent can then be acylated with a phenyl(alkyl) acid chloride, such as benzoyl chloride, and TEA in $CH_2Cl_2$ or can be submitted to a reductive amination procedure with a benzo-condensed cyclic ketone, for example 2-indanone, and $NaCNBH_3$ in methanol at room temperature (*J. Am. Chem. Soc.,* 1971, 93, 2897).

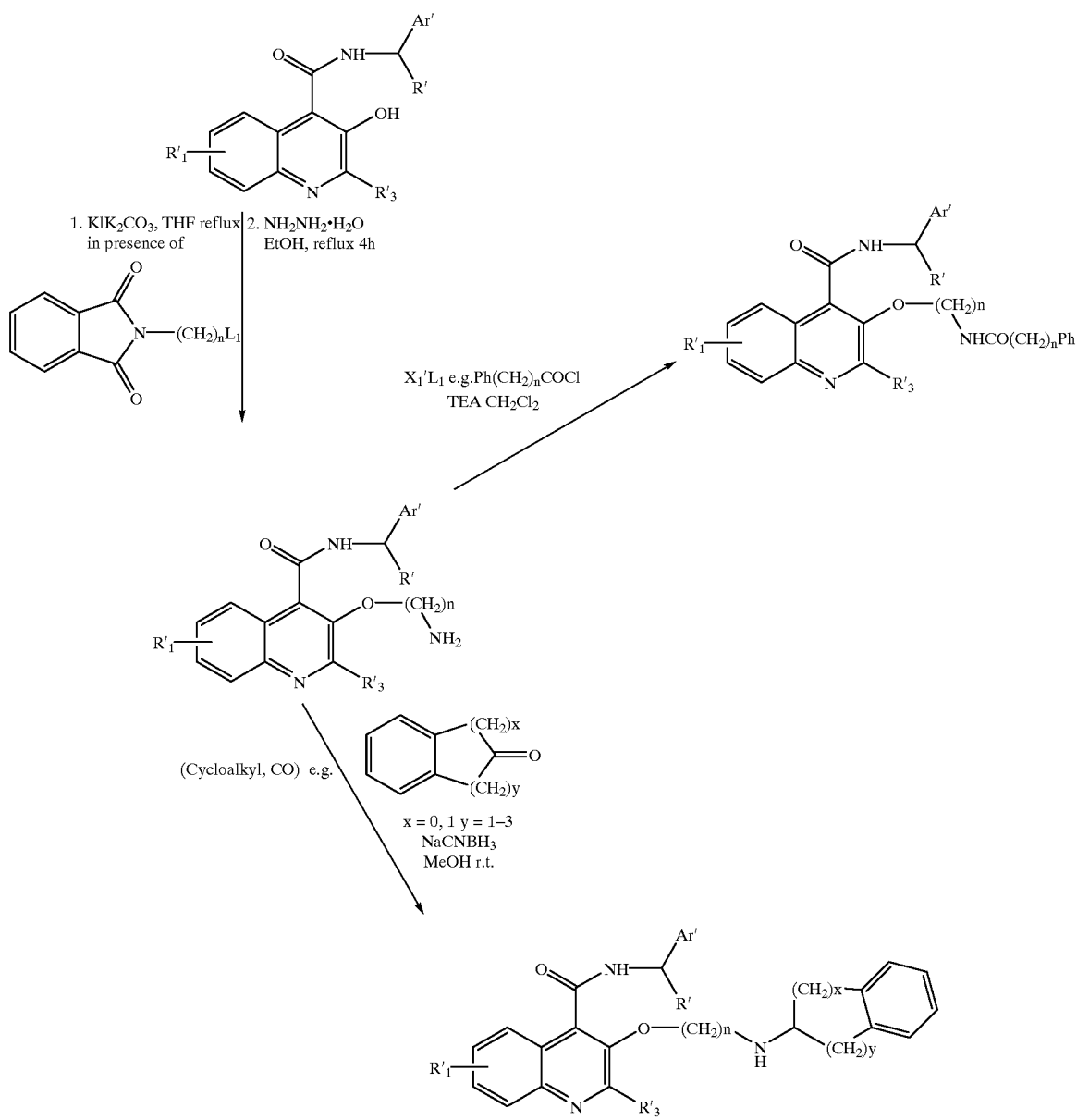

Scheme 3 wherein Ar', R', $R'_1$, $R'_2$ and $R'_3$ are as defined above, $X_1'$ is $X_1$ as defined in relation to formula (I) or a protected form thereof, (cyclic.CO) is a 5 to 9 membered single or fused ring cycloalkyl group wherein one or two ring atoms are optionally substituted with $C_{1-6}$ alkyl, said ring being optionally fused to a benzene ring and said ring also comprising an oxo group.

When $R'_2$ is $NH_2$, compounds (Ib) can be converted to other compounds of formula (I) or (Ib) as described in Scheme 4.

Scheme 4

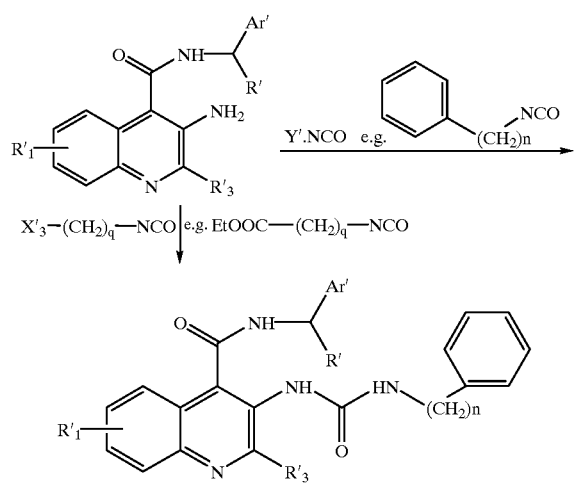

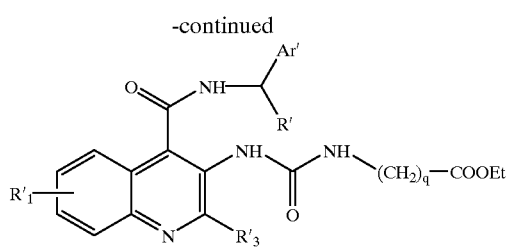

wherein Ar', R', $R'_1$, $R'_2$, $R'_3$ and n are as defined above, Y' is Y as defined in relation to formula (I) or a protected form thereof, $X_3'$ is $X_3$ as defined in relation to formula (I) or a protected form thereof and q is as defined in relation to formula (I). In particular, when $R'_2$ is $NH_2$, the phenyl(alkyl) ureido derivative is obtained by reaction with phenyl(alkyl) isocianate in $CH_2Cl_2/THF/CH_3CN$ at 40° C. In a similar way the ethoxycarbonylalkyl ureido derivatives are synthesized from the corresponding ethoxycarbonylalkyl isocianates in THF/DMF at 60° C. In a further aspect, the primary amine intermediate described in Scheme 3 (wherein $R_2$ is a moiety $—O—(CH_2)_n-N\ X_1X_2$ in which $X_1$ and $X_2$ both represent hydrogen) may be converted into a compound of formula (I) wherein one or both of $X_1$ and $X_2$ represent aryl-$C_{1-6}$-alkyl, heteroaryl-$C_{1-6}$-alkyl or a moiety $—CO—T—CO—T_1$ wherein T and $T_1$ are as defined in relation to formula (I), by using such reactions as those exemplified in Scheme 5:

Scheme 5

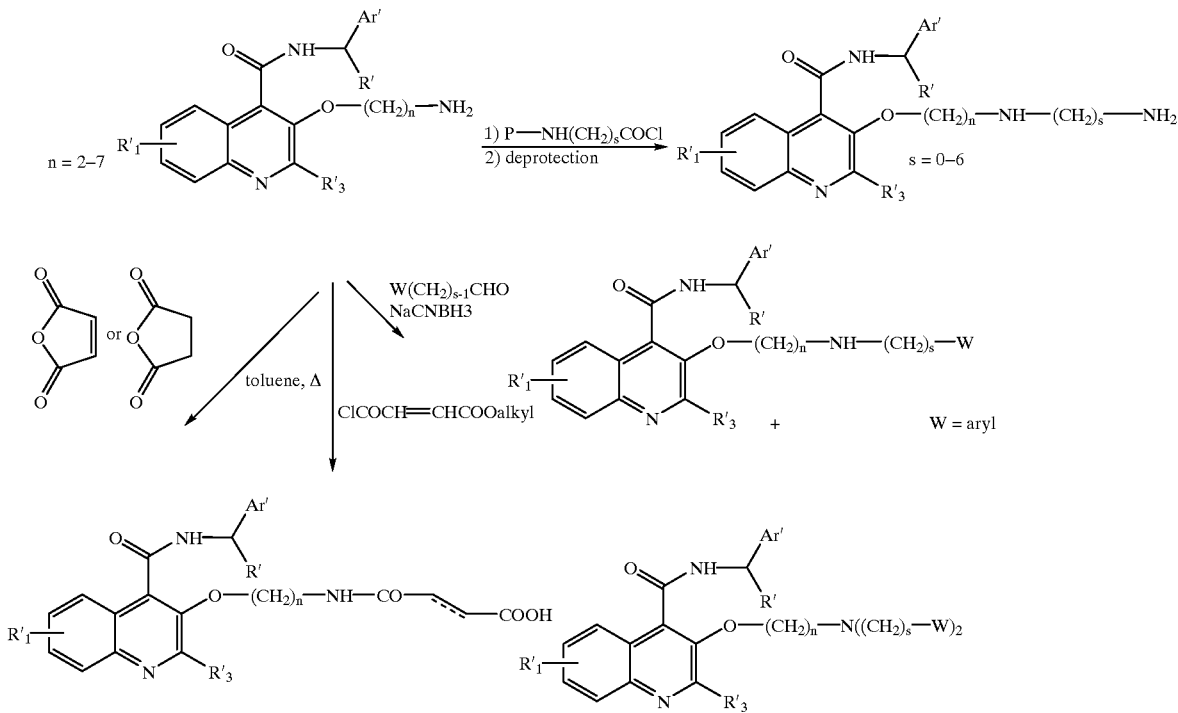

-continued

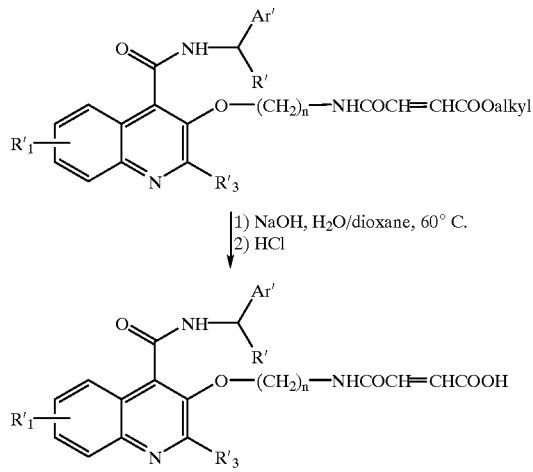

1) NaOH, H₂O/dioxane, 60° C.
2) HCl wherein Ar', R', R₁', and R₃' are as defined above.

Suitable conversion of one compound of formula (I) into another compound of formula (I) include conversion wherein one group R, R₁, R₂ or R₃ is converted into another group R, R₁, R₂ or R₃ respectively, said conversion conveniently proceeding via appropriate groups Ar', R', R'₁, R'₂ and R'₃ using conventional methodology, for example those methods described in Schemes 2, 3 and 4 above.

As mentioned before, the compounds of formula (I) may exist in more than one stereoisomeric form—and the process of the invention may produce racemates as well as enantiomerically pure forms. Accordingly, a pure enantiomer of a compound of formula (I) is obtained by reacting a compound of the above defined formula (II) with an appropriate enantiomerically pure primary amine of formula (IIIa) or (IIIc):

(IIIa)

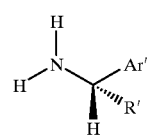

(IIIc)

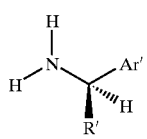

wherein R' and Ar' are as defined above, to obtain a compound of formula (I'a) or (I'c):

(I'a)

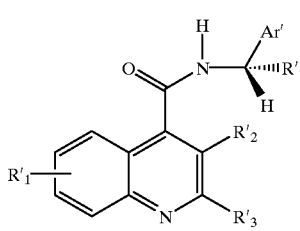

(I'c)

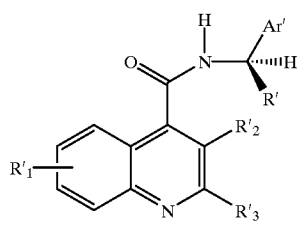

wherein Ar',R',R'₁,R'₂ and R'₃ are as defined above.

Compounds of formula (I'a) or (I'c) may subsequently be converted to compounds of formula (a) or (Ic):

(Ia)

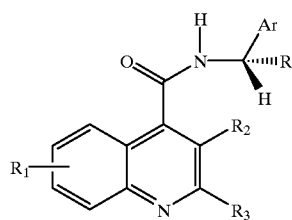

(Ic)

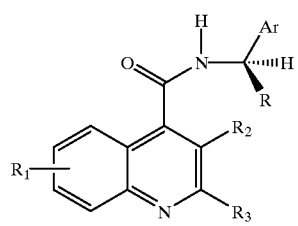

wherein Ar,R,R₁,R₂ and R₃ are as defined above by the methods of conversion mentioned before.

The compounds of formula (II) wherein R₂ is OH or NH₂ and protected forms of such compounds are either known compounds or they are prepared according to methods used to prepare known compounds, for example 3-hydroxy-2-phenyl-4-quinoline carboxylic acid (R₂ is OH, CAS=[485-89-2]) is prepared in accordance with the methods described in U.S. Pat. No. 2,776,290 (1957); and 3-amino-2-phenyl-4-quinoline carboxylic (R₂is NH₂, CAS=[36735-26-9]) is prepared in accordance with the methods described in Chemical Abstract 77:61769u (c.f. Khim. Geterotsikl. Soedin. (1972), 4, 525-6).

It will be appreciated that in any of the abovementioned reactions any reactive group in the substrate molecule may be protected according to conventional chemical practice.

Suitable protecting groups in any of the abovementioned reactions are those used conventionally in the art. Thus, for example suitable hydroxyl protecting groups include benzyl or trialkylsilyl groups. An amino group is conveniently protected as a (9-fluorenylmethoxycarbonyl)amino [FMOCamino] group.

The methods of formation and removal of such protecting groups are those conventional methods appropriate to the molecule being protected. Thus for example a benzyloxy group may be prepared by treatment of the appropriate compound with a benzyl halide, such as benzyl bromide, and thereafter, if required, the benzyl group may be conveniently removed using catalytic hydrogenation or a mild ether cleavage reagent such as trimethylsilyl iodide or boron tribromide. The FMOCamino group is prepared by reacting the amino compound with FMOC chloride in a solvent such as methylene chloride, preferably in the presence of triethylamine and usually at a low to ambient temperature, for example in the range of from 0° C. to ambient temperature. The FMOC group is removed by treating with an organic base such as diethylamine.

As indicated above, the compounds of formula (I) have useful pharmaceutical properties, accordingly the present invention also provides a compound of formula (I), or a pharmaceutically acceptable salt or solvate thereof, for use as an active therapeutic substance.

The present invention further provides a pharmaceutical composition comprising a compound of formula (I), or a pharmaceutically acceptable salt or solvate thereof, and a pharmaceutically acceptable carrier.

The present invention also provides the use of a compound of formula (I), or a pharmaceutically acceptable salt or solvate thereof, in the manufacture of a medicament for the treatment of the Primary and Secondary Conditions.

In addition as mentioned certain compounds of the invention are selective for the periphery. These compounds are characterised in that they are sufficiently hydrophilic so that substantially they do not pass through the blood-brain barrier: This hydrophilicity is readily measured by use conventional physiochemical methods, such as partition coefficient (logP and ΔLogP) measurements and is readily verified in vivo by for example the assessment of the relative level of compound in the plasma versus the brain after dosing to an animal.

Partition coefficients are determined by conventional methods such as those desclosed by A. Leo et al in Chem. Rev. 1971, 71, 525, R. C. Yound et al in J. Med. Chem. 1988, 31, 656 or by P. Seiler in Eur. J. Med. Chem. 1974, 9, 473.

Such a medicament, and a composition of this invention, may be prepared by admixture of a compound of the invention with an appropriate carrier. It may contain a diluent, binder, filler, disintegrant, flavouring agent, colouring agent, lubricant or preservative in conventional manner.

These conventional excipients may be employed for example as in the preparation of compositions of known agents for treating the conditions.

Preferably, a pharmaceutical composition of the invention is in unit dosage form and in a form adapted for use in the medical or veterinarial fields. For example, such preparations may be in a pack form accompanied by written or printed instructions for use as an agent in the treatment of the conditions.

The suitable dosage range for the compounds of the invention depends on the compound to be employed and on the condition of the patient. It will also depend, inter alia, upon the relation of potency to absorbability and the frequency and route of The compound or composition of the invention may be formulated for administration by any route, and is preferably in unit dosage form or in a form that a human patient may administer to himself in a single dosage. Advantageously, the composition is suitable for oral, rectal, topical, parenteral, intravenous or intramuscular administration. Preparations may be designed to give slow release of the active ingredient.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi- does forms such as a bottle from which the appropriate dose may be withdrawn or a solid form or concentrate which can be used to prepare an injectable formulation.

The compounds of this invention may also be administered by inhalation, via the nasal or oral routes. Such administration can be carried out with a spray formulation comprising a compound of the invention and a suitable carrier, optionally suspended in, for example, a hydrocarbon propellant.

Preferred spray formulations comprise micronised compound particles in combination with a surfactant, solvent or a dispersing agent to prevent the sedimentation of suspended particles. Preferably, the compound particle size is from about 2 to 10 microns.

A further mode of administration of the compounds of the invention comprises transdermal delivery utilising a skin-patch formulation. A preferred formulation comprises a compound of the invention dispersed in a pressure sensitive adhesive which adheres to the skin, thereby permitting the compound to diffuse from the adhesive through the skin for delivery to the patient. For a constant rate of percutaneous absorption, pressure sensitive adhesives known in the art such as natural rubber or silicone can be used.

As mentioned above, the effective dose of compound depends on the particular compound employed, the condition of the patient and on the frequency and route of administration. A unit dose will generally contain from 20 to 1000 mg and preferably will contain from 30 to 500 mg, in particular 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Alternatively the unit dose will contain from 2 to 20 mg of active ingredient and be administered in multiples, if desired, to give the preceding daily dose.

No unacceptable toxicological effects are expected with compounds of the invention when administered in accordance with the invention.

The present invention also provides a method for the treatment and/or prophylaxis of the Primary and Secondary Conditions in mammals, particularly humans, which comprise administering to the mammal in need of such treatment and/or prophylaxis an effective amount of a compound of formula (I) or a pharmaceutically acceptable salt or solvate thereof.

The activity of the compounds of the present invention, as $NK_3$ ligands, is determined by their ability to inhibit the binding of the radiolabelled $NK_3$ ligands, $[^{125}I]$-[Me—Phe$^7$]-NKB or $[^3H]$-Senktide, to guinea-pig and human $NK_3$ receptors (Renzetti et at, 1991, *Neuropeptide*, 18, 104–114; Buell et al, 1992, *FEBS*, 299(1), 90–95; Chung et al, 1994, *Biochem. Biophys. Res. Commun.*, 198(3), 967–972).

The binding assays utilized allow the determination of the concentration of the individual compound required to reduce by 50% the $[^{125}I]$-[Me—Phe$^7$]-NKB and $[^3H]$-Senktide specific binding to $NK_3$ receptor in equilibrium conditions (IC50).

Binding assays provide for each compound tested a mean $IC_{50}$ value of 2–5 separate experiments performed in duplicate or triplicate. The most potent compounds of the present invention show $IC_{50}$ values in the range 0.1–1000 nM. The $NK_3$-antagonist activity of the compounds of the present invention is determined by their ability to inhibit senktide-induced contraction of the guinea-pig ileum (Maggi et al, 1990, *Br. J. Pharmacol.*, 101, 996–1000) and rabbit isolated iris sphincter muscle (Hall et al., 1991, *Eur. J. Pharmacol.*, 199, 9–14) and human $NK_3$ receptors-mediated $Ca^{++}$ mobilization (Mochizuki et al, 1994, *J. Biol. Chem.*, 269, 9651–9658). Guinea-pig and rabbit in-vitro functional assays provide for each compound tested a mean $K_B$ value of 3–8 separate experiments, where $K_B$ is the concentration of the individual compound required to produce a 2-fold rightward shift in the concentration-response curve of senktide. Human receptor functional assay allows the determination of the concentration of the individual compound required to reduce by 50% ($IC_{50}$ values) the $Ca^{++}$ mobilization induced by the agonist NKB. In this assay, the compounds of the present invention behave as antagonists.

The therapeutic potential of the compounds of the present invention in treating the conditions can be assessed using rodent disease models.

As stated above, the compounds of formula (I) are also considered to be useful as diagnostic tool. Accordingly, the invention includes a compound of formula (I) for use as diagnostic tools for assessing the degree to which neurokinin-3 receptor activity (normal, overactivity or underactivity) is implicated in a patient's symptoms. Such use comprises the use of a compound of formula (I) as an antagonist of said activity, for example including but not restricted to tachykinin agonist-induced inositol phosphate turnover or electrophysiological activation, of a cell sample obtained from a patient. Comparison of such activity in the presence or absence of a compound of formula (I), will disclose the degree of NK-3 receptor involvement in the mediation of agonist effects in that tissue.

The following Descriptions illustrate the preparation of the intermediates, whereas the Examples illustrate the preparation of the compounds of the present invention. The compounds of the Examples are summarised in Table 1–3 below.

DESCRIPTION 1

(S)-N-(α-ethylbenzyl)-3-hydroxy-2-phenylquinoline-4-carboxamide 2.49 g (9.4 mmol) of 3-hydroxy-2-phenylquinoline-4-carboxylic acid (CAS [485-89-2]) were suspended in 150 ml of a 7/3 mixture of THF/CH$_3$CH; 1.40 g (10.3 mmol) of 1-hydroxybenzotriazole (HOBT) and 1.27 g (9.4 mmol) of (S)-α-ethylbenzylamine dissolved in 20 ml of CH$_2$Cl$_2$ were added and the reaction mixture was stirred at room temperature for 30 minutes. 2.13 g (10.3 mmol) of dicyclohexylcarbodiimide (DCC) dissolved in 20 ml of CH$_2$Cl$_2$ were added dropwise. The reaction was left at room temperature overnight, quenched with 20 ml of H$_2$O, evaporated in-vacuo to dryness and dissolved in EtOAc. The precipitated dicyclohexylurea was filtered off and the organic layer was washed with H$_2$O, 20% citric acid, sat. sol. NaHCO$_3$, sat. sol. NaCl. The organic layer was separated, dried over Na$_2$SO$_4$ and evaporated in-vacuo to dryness; the residue was purified by gradient column chromatography on 60–240 mesh silica gel using a mixture of hexane/EtOAc 9:1 as starting eluent and a mixture of hexane/EtOAc 7:3 as final eluent. The crude product was recrystallized from i-PrOH to yield 1.75 g of the title compound as a white solid.

$C_{25}H_{22}N_2O_2$

M.P.=168–168.4° C.

M.W.=382.47

[α]$_D^{20}$=−28.5 (c=0.5, MeOH)

Elemental analysis: Calcd. C, 78.51; H, 5.80; N, 7.33; Found C, 78.49; H, 5.84; N, 7.26.

I.R. (KBr): 3370; 1625; 1525 cm$^{-1}$.

300 MHz $^1$H-NMR (DMSO-d$_6$): δ 9.80 (s, 1H); 9.11 (d, 1H); 8.00-7.94 (m, 3H); 7.61-7.42 (m, 8H); 7.38 (dd, 2H); 7.28 (dd, 1H); 5.06 (dt, 1H); 1.82 (ddq, 2H); 0.97 (t, 3H).

MS (EI; TSQ 700; source 200 C;70 V;200 uA): 382 (M+); 264; 247; 219.

DESCRIPTION 2

(S)-N-(α-ethylbenzyl)-3-amino-2-phenylquinoline-4-carboxamide 1.5 g (5.7 mmol) of 3-amino-2-phenylquinoline-4-carboxylic acid (CAS [36735-26-9]) were dissolved in 140 ml of a 7/3 mixture of THF/CH$_3$CN; 1.5 g (11.1 mmol) of 1-hydroxybenzotriazole (HOBT) were added and 1.15 g (8.5 mmol) of (S)-α-ethyl benzylamine dissolved in 10 ml of CH$_2$Cl$_2$ were added dropwise. After cooling of the reaction mixture to 0° C., 1.4 g (6.7 mmol) of dicyclohexylcarbodiimmide (DCC) dissolved in 10 ml of CH$_2$Cl$_2$ were added dropwise. The solution was kept at 0° C. for 30 minutes and then at room temperature overnight. The reaction mixture was evaporated in-vacuo, the residue was dissolved in CH$_2$Cl$_2$ and the solution filtered off, washed with H$_2$O, 20% citric acid, sat. sol. NaHCO$_3$ and sat. sol. NaCl. The organic layer was separated, drive over Na$_2$SO$_4$ and evaporated in-vacuo to dryness to obtain 2.4 g of the crude product. This was triturated with i-Pr$_2$O, then recrystallized with a 10:1 mixture of iPr$_2$O/i-PrOH to yield 1.7 g of the title compound.

$C_{25}H_{23}N_3O$

M.P.=153–155° C.

M.W.=381.48

[α]$_D^{20}$=−68.0 (c=0.5, MeOH)

Elemental analysis: Calcd. C, 78.71;H,6.08;N,11.01; Found C, 78.45;H,6.10;N,10.96.

I.R. (KBr): 3490; 3380; 3260; 1630; 1600 cm$^{-1}$

300 MHz $^1$H-NMR (DMSO-d$_6$): δ 9.20 (d, 1H); 7.87 (m, 1H); 7.70 (d, 2H); 7.59-7.26 (m, 11H); 5.08 (dt, 1H); 4.80 (s br, 2H); 2.81 (dq, 2H); 0.95 (t, 3H).

MS (EI; TSQ 700; source 200 C;70 V;200 uA):381 (M+.); 352; 247; 219; 218.

DESCRIPTION 3

(S)-N-(α-ethylbenzyl)-2-phenyl-3-(2-phthalimidoethoxy)quinoline-4-carboxamide 1.90 g (5.0 mmol) of (S)-N-(α-ethylbenzyl)-3-hydroxy-2-phenylquinoline-4-carboxamide (product of Description 1) were dissolved in 20 ml of THF. 3.80 g (14.9 mmol) of N-(2-bromoethyl)phthalimide dissolved in 15 ml of THF, 2.00 g (14.5 mmol) of K$_2$CO$_3$ and 0.25 g of KI were added and the suspension was stirred at room temperature for 2.5 hours and then refluxed for 2 hours. Additional 1.90 g (7.4 mmol) of N-(2-bromoethyl)phthalimide and a catalytic amount of KI were added and the reaction refluxed for 3.5 hours; additional 0.50 g (2.0 mmol) of N-(2-bromoethyl) phthalimide and a catalytic amount of KI were added and the reaction refluxed for 5 hours.

The inorganic salts were filtered off and the reaction mixture evaporated in-vacuo to dryness, dissolved in CH$_2$Cl$_2$ and washed with water; the organic layer was separated, dried over Na$_2$SO$_4$ and evaporated in-vacuo to dryness. The residue was purified by flash column chromatorgraphy on 230–400 mesh silica gel, eluting initially with a mixture of hexane/ethyl acetate 8:2 containing 0.5% NH$_4$OH (28%) and then with a mixture of hexane/ethyl acetate 3:2 containing 0.5% NH$_4$OH (28%). The purified solid obtained (2.60 g) was triturated with i-Pr$_2$O, filtered, washed and dried to yield 2.5 g of the title compound.

$C_{35}H_{29}N_3O_4$

M.P.=172–175° C.

M.W.=555.64

[α]$_D^{20}$=−16.3 (c=0.5, MeOH) *I.R. (KBr):* 3280; 3060; 2960; 1780; 1715; 1660; 1530 cm$^{-1}$.

300 MHz $^1$H-NMR (DMSO-d$_6$): δ 9.27 (d, 1H); 8.03 (d, 1H); 7.92-7.84 (m, 4H); 7.78-7.69 (m, 3H); 7.60-7.53 (m, 2H); 7.46-7.38 (m, 4H); 7.27 (dd, 1H); 7.13-7.04 (m, 3H); 4.96 (dt, 1H); 3.92- 3.78 (m, 2H); 3.72-3.55 (m, 2H); 1.78 (dq, 2H); 0.93 (t, 3H).

MS (EI; TSQ 700; source 180 C;70 V; 200 uA): 555 (M+.), 526, 421, 174.

DESCRIPTION 4

(S)-N-(α-ethylbenzyl)-3-(2-aminoethoxy)-2-phenylquinoline-4-carboxamide 2.2 g (3.9 mmol) of (S)-N-(α-ethylbenzyl)-2-phenyl-3-(2-phthalimidoethoxy) quinoline-4-carboxamide (compound of Description 3) were dissolved in 150 ml of 96% EtOH; the solution was heated to reflux; 0.38 ml (7.8 mmol) of hydrazine hydrate were added and the reaction mixture refluxed for 4 hours. Additional 0.4 ml (8.2 mmol), 0.2 ml (4.1 mmol), 0.2 ml (4.1 mmol), 0.4 ml (8.2 mmol), 0.4 ml (8.2 mmol) of hydrazine hydrate were added every 12 hours while refluxing the reaction mixture. Then it was evaporated in-vacuo to dryness and 20 ml of H$_2$O were added; it was cooled with an ice bath and 10 ml of conc. HCl were added. The reaction mixture was refluxed for 1 hour and then, after cooling, the phthalhydrazide was filtered off. The resulting aqueous filtrate was washed with EtOAc, basified with 2N NaOH and extracted with EtOAc. The organic layer was washed with sat. sol. NaCl, dried over Na$_2$SO$_4$ and evaporated in-vacuo to dryness. The residue was purified by flash column chromatography on 230–400 mesh silica gel, eluting with a mixture of EtOAc/MeOH 96:4 containing 1.2% NH$_4$Oh (28%) to yield 1.2 g of the title compound.

$C_{27}H_{27}N_3O_2$

M.P. =62–66° C.

M.W.=425.54

I.R. (KBr): 3360; 3250; 3060; 3020; 2960; 2920; 2870; 1640; 1540 cm$^{-1}$.

300 MHz $^1$H-NMR (DMSO-d$_6$): δ 9.45 (d, 1H); 8.09 (d, 1H); 8.00 (dd, 1H); 7.94 (s br, 3H); 7.76 (ddd, 1H); 7.65-7.51 (m, 4H); 7.48-7.40 (m, 3H); 7.31 (dd, 1H); 5.09 (dt, 1H); 3.83 (t, 2H); 2.72 (m, 2H); 1.93-1.80 (m, 2H); 0.99 (t, 3H).

MS (FAB POS; thioglycerine matrix; FAB gas Xe; 8 kV; source 50): 426 (MH+).

EXAMPLE 1

(S)-N-(α-ethylbenzyl)-3-(ethoxycarbonylmethoxy)-2-phenylquinoline-4-carboxamide 2.0 g (5.2 mmol) of (S)-N-(α-ethylbenzyl)-3-hydroxy-2-phenylquinoline-4-carboxamide (compound of Description 1) were dissolved, under nitrogen atmosphere and magnetic stirring, in 20 ml of THF. 2.0 g (14.5 mmol) of K$_2$CO$_3$, 0.87 ml (7.8 mmol) of ethyl bromoacetate and a small amount of Ki were added and the reaction mixture was left at room temperature under magnetical stirring for 2.5 hours. The precipitate was filtered off and the solution was evaporated in-vacuo to dryness; the residue was dissolved in water and extracted with EtOAc; the organic phase was separated, dried over Na$_2$SO$_4$ and evaporated in-vacuo to dryness to obtain 3.3 g of a dense yellow oil. The oil was purified by flash chromatography on 230–400 mesh silica gel, eluting with a mixture of hexane/EtOAc 70:30 containing 0.5% of 28% NH$_4$OH, and the purified product was triturated with i-Pr$_2$O/i-PrOH to yield 2.1 g of the title compound as a white solid.

C$_{29}$H$_{28}$N$_2$O$_4$

M.P.=103–105° C.

M.W.=468.56

$[\alpha]_D^{20}$=−42.5 (c=0.5, MeOH)

Elemental analysis: Calcd. C, 74.34;H, 6.02;N, 5.98; Found C, 74.4;H, 6.01;N, 6.00.

I.R. (KBr): 3320-3140; 3100-3020; 2980-2920; 1758; 1630; 1550 cm$^{-1}$.

300 MHz $^1$H-NMR (DMSO-d$_6$): δ 9.28 (d, 1H); 8.80 (d, 1H); 8.05-7.98 (m, 2H); 7.80-7.71 (m, 1H); 7.60 (d, 2H); 7.55-7.48 (m, 3H); 7.43 (d, 2H); 7.35 (dd, 2H); 7.28 (dd, 1H); 5.06 (dt, 1H); 4.26 (ABq, 2H); 4.04 (q, 2H); 1.86-1.67 (m, 2H); 1.12 (t, 3H); 0.96 (t, 3H).

MS (EI; TSQ 700; source 180 C;70V; 200 uA): 468 (M+.); 439; 334; 306; 278.

EXAMPLE 2

(S)-N-(α-ethylbenzyl)-3-(carboxymethoxy)-2-phenylquinoline-4-carboxamide hydrochloride 0.35 g (0.7 mmol) of (S)-N-(α-ethylbenzyl)-3-(ethoxycarbonylmethoxy)-2-phenyl quinoline-4-carboxamide (compound of Example 1) were dissolved in 20 ml of 37% HCl and the reaction mixture was refluxed under magnetical stirring for 20'. The solution was evaporated in-vacuo to dryness and the crude product was triturated with warm EtOAc/i-PrOH to yield 0.17 g of the title compound as a white solid.

C$_{27}$H$_{24}$N$_2$O$_4$.HCl

M.P.=203–204° C.

M.W.=476.96

$[\alpha]_D^{20}$=−30.2 (c=0.5, MeOH)

Elemental analysis: Calcd. C, 67.99;H, 5.28;N, 5.87; Found C, 67.44;H,5.29;N, 5.84.

I.R. (Nujol): 3280-3120; 3100-3000; 1740; 1670; 1635; 1545 cm$^{-1}$.

300 MHz $^1$H-NMR (DMSO-d$_6$): δ 9.30 (d, 1H); 8.11-8.01 (m, 3H); 7.80-7.71 (m, 1H); 7.59 (d, 2H); 7.56-7.48 (m, 3H); 7.44 (d, 2H); 7.36 (dd, 2H); 7.27 (dd, 1H); 5.07 (dt, 1H); 4.26 (ABq, 2H); 1.81 (dq, 2H); 0.97 (t, 3H).

MS (EI; TSQ 700; source 180 C; 70 V;200 uA): 440 (M+); 411; 396; 306; 278.

EXAMPLE 3

(S)-N-(α-ethylbenzyl)-3-(aminocarbonylmethoxy)-2-phenyquinoline-4-carboxamide 0.5 g (1.3 mmol) of (S)-N-(α-ethylbenzyl)-3-hydroxy-2-phenylquinoline-4-carboxamide (compound of Description 1) were dissolved, under nitrogen atmosphere and magnetic stirring, in 5 ml of THF; 0.5 g (3.6 mmol) of K$_2$CO$_3$, 0.27 g (1.9 mmol) of 2-bromoacetamide and a small amount of KI were added. The reaction mixture was left overnight under magnetical stirring; the precipitate was filtered off and the residue dissolved in H$_2$O and extracted with EtOAc; the organic layer was washed with sat. sol. NaCl, dried over Na$_2$SO$_4$ and evaporated in-vacuo to dryness. The crude product was triturated with hexane and then recrystallized form EtOH to yield 0.29 g of the title compound as a white solid.

C$_{27}$H$_{25}$N$_3$O$_3$

M.P.=237–240° C.

M.W.=439.51

$[\alpha]_D^{20}$=−35.9 (c=0.5, MeOH)

Elemental analysis: Calcd. C. 73.78;H, 5.73;N, 9.56; Found C, 73.75;H,5.75;N, 9.54.

I.R. (KBr): 3440; 3310; 3220; 3100-3020; 2980-2920; 1688; 1650; 1550 cm$^{-1}$.

300 MHz $^1$H-NMR (DMSO-d$_6$): δ 9.30 (d, 1H); 8.08 (d, 1H); 8.05-8.00 (m, 2H); 7.80-7.70 (m, 1H); 7.60 (d, 2H); 7.57-7.50 (m, 3H); 7.43 (d, 2H); 7.38 (dd, 2H); 7.37 (s br, 1H); 7.28 (dd, 1H); 7.12 (s br, 1H); 5.07 (dt, 1H); 4.03 (ABq, 2H); 1.81 (m, 2H); 0.80 (t, 3H).

MS (EI; TSQ 700; source 180 C;70 V; 200 uA): 439 (M+); 410; 305; 277; 248.

EXAMPLE 4

(S)-N-(α-ethylbenzyl)-3-(diemthylaminocarbonylmethoxy)-2-phenylquinoline-4-carboxamide 0.6 g (1.3 mmol) of (S)-N-(α-ethylbenzyl)-3-(ethoxycarbonylmethoxy)-2-phenyl quinoline-4-carboxamide (compound of Example 1) were dissolved in 30 ml of Me$_2$NH/EtOH (~28%); a small amount of NaCN was added and the reaction mixture was heated in a Parr apparatus to 100° C. (external temperature) for 2 hours, then to 120° C. for 12 hours. The reaction mixture was evaporated in-vacuo to dryness, the residue was dissolved in EtOAc and washed with H$_2$O, 20% citric acid, sat. sol. NaHCO$_3$ and sat. sol. NaCl. The organic layer was dried over Na$_2$SO$_4$ and evaporated in-vacuo to dryness to obtain 0.45 g of a residue which was flash chromatographed on 230–400 mesh silica gel, eluting with a mixture of hexane/EtOAc 50:50 containing 0.5% of 28% NH$_4$OH. The crude product was triturated with Et$_2$O, filtered, washed and dried to yield 80 mg of the title compound as a white solid.

C$_{29}$H$_{29}$N$_3$O$_3$

M.P.=86–88° C.

M.W.=467.57

$[\alpha]_D^{20}$=−41.2 (c=0.25, MeOH)

I.R. (KBr): 3240; 3060; 2980-2820; 1685; 1625; 1550 cm$^{-1}$.

300 MHz $^1$H-NMR (DMSO-d$_6$): δ 9.40 (d, 1H); 8.04 (m, 3H); 7.72 (ddd, 1H); 7.65-7.74 (m, 5H); 7.44 (d, 2H); 7.26 (dd, 2H); 7.28 (dd, 1H); 5.05 (dt, 1H); 4.43 (ABq, 2H); 2.70 (s, 3H); 2.50 (s, 3H); 1.80 (m, 2H); 0.94 (t, 3H).

MS (EI; TSQ 700; source 180 C;70 V;200 uA): 467 (M+); 438; 333; 305; 262.

EXAMPLE 5

(S)-N-(α-ethylbenzyl)-3-(ethoxycarbonyloxy)-2-phenylquinoline-4-carboxamide 0.5 g (1.3 mmol) of (S)-N-(α-ethylbenzyl)-3-hydroxy-2-phenylquinoline-4-carboxamide (compound of Description 1) were dissolved in 10 ml of pyridine; 0.5 ml (5.2 mmol) of ethyl chloroformate were added dropwise and the solution was refluxed under magnetical stirring for 8 hours. The reaction mixture was allowed to reach room temperature and left overnight. 1.0 ml (10.4 mmol) of ethyl chloroformate were added and the solution refluxed for 4 hours. The pyridine was evaporated off with toluene; the residue was dissolved in $CH_2Cl_2$, washed with $H_2O$ and the organic layer dried over $na_2SO_4$ and evaporated in-vacuo to dryness. The crude product was triturated with warm i-$Pr_2O$ to yield 0.25 g of the title compound as a yellow solid.

$C_{28}H_{26}N_2O_4$

M.P.=119–121° C.

M.W.=454.53

$[\alpha]_D^{20}$=−57.8 (c=0.25, MeOH)

I.R. (Nujol): 3280; 1765; 1645; 1550 $cm^{-1}$.

300 MHz $^1$H-NMR (DMSO-$d_6$): δ 9.30 (d, 1H); 8.15 (d, 1H); 7.89-7.77 (m, 3H); 7.70 (m, 2H); 7.59-7.49 (m, 3H); 7.42 (d, 2H); 7.33 (dd, 2H); 7.28 (dd, 1H); 5.05 (dt, 1H); 3.93 (q, 2H); 1.78 (m, 2H); 0.97 (t, 1H); 0.95 (t, 1H).

MS (EI; TSQ 700; source 180 C;70 V;200 uA): 454 (M+); 425; 382; 320; 247; 219.

EXAMPLE 6

(S)-N-(α-ethylbenzyl)-3-(3-phenylureido)-2-phenylquinoline-4-carboxamide 1.5 g (3.9 mmol) of (S)-N-(α-ethylbenzyl)-3-amino-2-phenylquinoline-4-carboxamide (compound of Description 2) were dissolved in 30 ml of dry $CH_2Cl_2$, 10 ml of dry THF and 10 ml of dry $CH_3CN$. 0.47 ml (4.3 mmol) of phenylisocyanate dissolved in 10 ml of $CH_2Cl_2$ were added and the reaction mixture heated to 40° C. for 4 hours. After cooling of the reaction mixture, the precipitate was collected by filtration and washed with $CH_2Cl_2$ to yield 0.9 g of the title compound.

$C_{32}H_{28}N_4O_2$

M.P.=257–258° C.

M.W.=500.61

$[\alpha]_D^{20}$=−64.5 (c=0.25, DMF)

I.R. (KBr): 3250; 3060; 2960; 1680; 1600; 1550 $cm^{-1}$.

300 MHz $^1$H-NMR (DMSO-$d_6$): δ 9.06 (d, 1H); 8.71 (s br, 1H); 8.13-8.05 (m, 2H); 7.83-7.69 (m, 4H); 7.62 (dd, 1H); 7.48-7.35 (m, 5H); 7.23-7.10 (m, 7H); 6.91 (m, 1H).

MS (FAB POS; matrix thioglicerine; FAB gas Xe; 8 kV; source 50): 501 (MH+).

EXAMPLE 7

(S)-N-(α-ethylbenzyl)-3-(3-ethoxycarbonylmethylureido)-2-phenylquinoline-4-carboxamide 2.0 g (5.2 mmol) of (S)-N-(α-ethylbenzyl)-3-amino-2-phenylquinoline-4-carboxamide (compound of Description 2) were dissolved in 10 ml of dry THF and 5 ml of dry DMF. 1.71 ml (15.2 mmol) of phenylisocyanate neat were added and the reaction mixture heated to 60° C. for 3 days; 1.0 ml (10.3 mmol) of phenylisocyanate neat were added again and the reaction mixture stirred at 60° C. for additional 2 days. After cooling of the reaction mixture, the precipitate was collected by filtration and washed with $CH_2Cl_2$ to yield 0.8 g of a white powder. The residue was recrystallized from toluene containing traces of EtOH and then from EtOH containing traces of $H_2O$ to yield 0.45 g of the title compound.

$C_{30}H_{30}N_4O_4$

M.P.=237–238° C.

M.W.=510.60

$[\alpha]_D^{20}$=−45 (c=0.1, DMF)

I.R. (KBr): 3360; 3310; 3250; 3060; 2960; 1740; 1655; 1560 $cm^{-1}$.

300 MHz $^1$H-NMR (DMSO-$d_6$): δ 8.83 (d, 1H); 8.16 (s, 1H); 8.06 (d, 1H); 7.80-7.70 (m, 3H); 7.66-7.54 (m, 2H); 7.50-7.23 (m, 8H); 6.60 (t br, 1H); 5.00 (dt, 1H); 4.09 (q, 2H); 3.66 (m, 2H); 1.75 (m, 2H); 1.19 (t, 3H); 0.90 (t, 3H).

MS (EI; TSQ 700;source 180 C;80 V;200 uA): 510 (M+); 407; 290.

EXAMPLE 8

(S)-N-(α-ethylbenzyl)-3-[2-(2-indanylamino)ethoxy]-2-phenylquinoline-4-carboxamide hydrochloride 1.0 g (2.3 mmol) di (S)-N-(α-ethylbenzyl)-3-(2-aminoethoxy)-2-phenylquinoline-4-carboxamide (compound of Description 4) were dissolved, under nitrogen atmosphere and magnetical stirring, in 15 ml of MeOH; 0.47 g (3.5 mmol) of 2-indanone and a small amount of triturated molecular sieves were added and the mixture was stirred at room temperature for 30 minutes. 0.15 g (2.3 mmol) of $NaCNBH_3$ were added portionwise over 30 minutes and the mixture was left under stirring at room temperature overnight. The reaction was quenched with 20 ml of 2N NaOH and, after stirring at room temperature for 20 minutes, was evaporated in-vacuo to dryness. The residue was dissolved in 2N NaOH and extracted with $CH_2Cl_2$; the organic layer was washed with sat. sol. NaCl and extracted with 20% citric acid. The acid aqueous layer was basified with conc. NaOH and extracted with EtOAc; the organic layer was washed several times with sat. sol. NaCl, dried over $Na_2SO_4$, and evaporated in-vacuo to dryness to obtain 1.0 g of the title compound as free base. This was dissolved in EtOAc and the solution acidified with HCl/$Et_2O$ to yield 0.84 g of the corresponding hydrochloride, which was recrystallized from acetone/EtOH to obtain 0.49 g of the title compound as a white powder.

$C_{36}H_{35}N_3O_2 \cdot HCl$

M.P.=156–160° C.

M.W.=578.16

$[\alpha]_D^{20}$=−11.0 (c=0.5, MeOH)

I.R. (KBr): 3700-3250; 3240-3100; 3080-2900; 2850-2000; 1670-1630; 1550 $cm^{-1}$.

300 MHz $^1$H-NMR (DMSO-$d_6$): δ 9.52 (d, 1H); 9.40 (s br, 1H); 8.10 (d, 1H); 7.97 (dd, 2H); 7.81-7.73 (m, 1H); 7.65-7.19 (m, 14H); 5.05 (dt,1H); 3.98 (m, 2H); 3.69 (m, 1H); 3.18-3.06 (m, 2H); 3.02-2.80 (m,4 H); 1.94-1.74 (m, 2H); 0.96 (t, 3H).

MS (FAB POS; matrix thioglicerine; FAB gas Xe; 8 kV; source 50 C): 542 (MH+).

EXAMPLE 9

(S)-N-(α-ethylbenzyl)-3-(2-benzoylaminoethoxy)-2-phenylquinoline-4-carboxamide 0.95 g (2.2 mmol) of (S)-N-(α-ethylbenzyl)-3-(2-aminoethoxy)-2-phenylquinoline-4-carboxamide (compound of Description 4) were dissolved, under nitrogen atmosphere and magnetical stirring, in 12 ml of dry $CH_2Cl_2$; 0.37 ml (2.6 mmol) of TEA were added, the solution cooled to 0° C. and 0.3 ml (2.6 mmol) of benzoyl chloride, dissolved in in 3 ml dry $CH_2Cl_2$ were added dropwise. The reaction was left 30 minutes at 0° C., then allowed to reach room temperature and left overnight. The mixture was evaporated in-vacuo to dryness, the residue was dissolved in $CH_2Cl_2$, and washed with $H_2O$, 20% citric acid, sat. sol. $NaHCO_3$, sat. sol. NaCl; the organic layer was dried over $Na_2SO_4$ and evaporated in-vacuo to dryness. The residue was triturated with hot i-$Pr_2O$/i-PrOH to yield 0.8 g of the title compound as a white solid.

$C_{34}H_{31}N_3O_3$

M.P.=157–160° C.

M.W.=529.64

$[\alpha]_D^{20}$=−27.3 (c=0.5, MeOH)

Elemental analysis: Calcd. C, 77.10; H, 5.90; N, 7.93; Found C, 76.92; H, 5.88; N, 7.88;

I.R.(KBr): 3300; 3240; 3100-3020; 2980-2920; 1632; 1545 $cm^{-1}$.

300 MHz $^1$H NMR (DMSO-$d_6$) δ 9.31 (d, 1H); 8.32 (t, 1H); 8.05 (d, 1H); 7.90 (m, 2H); 7.79-7.69 (m, 3H); 7.60-7.33 (m, 12H); 7.29 (dd,1H); 5.05 (dt,1H); 3.80 (m, 2H); 3.42-3.29 (m, 1H); 3.25-3.15 (m, 1H); 1.89-1.72 (m, 2H); 0.93 (t, 3H).

MS (EI; TSQ 700; source 180 C; 10 V; 200 uA): 529 (M+); 382; 148

DESCRIPTION 5 methyl-3-chlorocarbonylpropenoate 5.0 g (51.0 mmol) of maleic anhydride were heated to 100° C. in 2.2 ml of MeOH for 1 hour [*J. Chem. Soc.*, 1964, 526–528]. The reaction mixture was cooled to room temperature and 37 ml (50.7 mmol) of $SOCl_2$ were added dropwise. The reaction was refluxed for 1.5 hours and then distilled collecting the fraction boiling at 42–44° C./2 mbar to obtain 5.3 g of the title compound, possibly as a mixture of E and Z diastereoisomers. This compound was used without further purification in the subsequent reaction to prepare Examples 18 and 19.

EXAMPLE 10

(S)-N-(a-ethylbenzyl)-3-[3-ethoxycarbonyl)-propoxy]-2-phenylquinoline-4-carboxamide 2.0 g (5.23 mmol) of (S)-N-(α-ethylbenzyl)-3-hydroxy-2-phenylquinoline-4-carboxamide (compound of Description 1), 2.17 g (15.70 mmol) of $K_2CO_3$, 0.26 g (1.57 mmol) of KI and 1.13 ml (7.84 mmol) of ethyl 4-bromobutyrate were suspended in 50 ml of dry THF and the reaction was stirred at room temperature for 24 hours. The solid was filtered off and the solvent was evaporated in vacuo to dryness. The residue was dissolved in $CH_2Cl_2$ and the organic phase was washed with $H_2O$, separated, dried over $Na_2SO_4$ and evaporated in vacuo to dryness. The crude product was triturated with hot i-$Pr_2O$ to yield 2.10 g of the title compound as a white powder.

$C_{31}H_{32}N_2O_4$

M.P.=140–142° C.

M.W.=496.61

$[\alpha]_D^{20}$=−41.6 (c=1, MeOH)

I.R.(KBr): 3110; 2960-2850; 1740; 1650 $cm^{-1}$.

300 MHz $^1$H NMR (DMSO-$d_6$) δ 9.25 (d, 1H); 8.06 (d, 1H); 7.92 (dd, 2H); 7.72 (ddd, 1H); 7.63-7.50 (m, 5H); 7.44 (d, 2H); 7.39 (dd,2H); 7.28 (dd, 1H); 5.08 (dt, 1H); 3.99 (q, 2H); 3.61 (m, 2H); 2.15-1.98 (m, 2H); 1.90-1.74 (m, 2H); 1.60-1.51 (m, 2H); 1.16 (t, 3H); 0.98 (t, 3H).

MS (EI; TSQ 700; source 180 C;70 V; 200 uA): 496 (M+); 115.

EXAMPLE 11

(S)-N-(a-ethylbenzyl)-3-(carboxypropoxy)-2-phenylquinoline-4-carboxamide 0.6 g (1.21 mmol) of (S)-N-(a-ethylbenzyl)-3-[3-ethoxycarbonyl)propoxy]-2-phenylquinoline-4-carboxamide (compound of Example 10) were dissolved in 30 ml of 6N HCl and the solution was refluxed for 4 hours. The reaction mixture was evaporated in vacuo to dryness and the crude compound was recrystallized from toluene with traces of THF to yield 0.5 g of the title compound as a yellow solid.

$C_{29}H_{28}N_2O_4$

M.P.=149–151° C.

M.W.=468.56

$[\alpha]_D^{20}$=−42.3 (c=1, MeOH)

I.R.(KBr): 3249; 3065; 2971-2840; 1709; 1633; 1544 $cm^{-1}$.

300 MHz $^1$H NMR (DMSO-$d_6$) δ 11.98 (s, 1H); 9.24 (d, 1H); 8.07 (d, 1H); 7.93 (dd, 2H); 7.72(ddd, 1H); 7.61-7.50 (m, 5H); 7.44 (d, 2H); 7.38 (dd, 2H); 7.28 (dd, 1H); 5.08(dt, 1H); 3.62 (m, 2H); 2.01 (m, 2H); 1.90-1.72 (m, 2H); 1.55 (m, 2H); 0.99 (t, 3H).

MS (EI; TSQ 700; source 180 C;70 V; 200 uA): 468 (M+); 439; 382; 334; 264; 247; 219; 134; 119; 91.

EXAMPLE 12

(S)-N-(a-ethylbenzyl)-3-[2-(2'-hydroxymethylphenylacetyl)aminoethoxy]-2-phenylquinoline-4-carboxamide 0.7 g (4.7 mmol) of isochromanone were dissolved in 25 ml of abs. EtOH; 2.0 g (4.7 mmol) of (S)-N-(α-ethylbenzyl)-3-(2-aminoethoxy)-2-phenylquinoline-4-carboxamide (compound of Description 4) were added and the reaction was refluxed for 12 hours. Additional 0.3 g (2.0 mmol) of isochromanone were added and the reaction mixture was refluxed for 5 hours; additional 0.5 g (3.4 mmol) of isochromanone were added and the reaction refluxed for 10 hours. After cooling, it was evaporated in vacuo to dryness and the residue was purified by gradient flash column chromatography on 230–400 mesh silica gel utilising a mixture of hexane/EtOAc 50:50 containing 0.5% $NH_4OH$ (28%) as starting eluent and a mixture of hexane/EtOAc 20:80 containing 0.5% $NH_4OH$ (28%) as final eluent. The crude product so obtained was triturated with i-$Pr_2O$/i-PrOH to yield 1.8 g of the title compound.

$C_{36}H_{35}N_3O_4$

M.P.=160–163° C.

M.W.=573.69

$[\alpha]_D^{20}$=−31.5 (c=0.5, MeOH)

Elemental analysis: Calcd. C, 75.36; H, 6.15; N, 7.32; Found C, 75.09; H, 6.14; N, 7.34

I.R.(KBr): 3600-3100; 3100-3000; 1641; 1558 $cm^{-1}$.

300 MHz $^1$H NMR (DMSO-$d_6$) δ 9.30 (d, 1H); 7.98 (m, 2H); 7.89 (t br 1H); 7.73 (ddd, 1H); 7.59(m, 2H); 7.57-7.48 (m, 3H); 7.45 (m, 2H); 7.41-7.33 (m, 3H); 7.28 (dd, 1H); 7.19 (dd, 1H); 7.15 (dd, 1H); 7.09 (dd, 1H); 5.09 (t, 1H); 5.08 (dt, 1H); 4.48 (d, 1H); 3.70-3.59 (m, 2H); 3.37 (s, 2H); 3.12-2.92 (m, 2H); 1.90-1.75 (m, 2H); 0.99 (t, 3H).

MS (EI; TSQ 700; source 180 C;70 V; 200 uA): 555; 438; 411; 382; 247; 218; 192; 174; 119.

EXAMPLE 13

(S,Z)-N-(a-ethylbenzyl)-3-[2-(3-carboxypropenoyl) aminoethoxy]-2-phenylquinoline-4-carboxamide 2.0 g (4.7 mmol) of (S)-N-(α-ethylbenzyl)-3-(2-aminoethoxy)-2-phenylquinoline-4-carboxamide (compound of Description 4) and 0.61 g (6.2 mmol) of maleic anhydride were dissolved in 50 ml of toluene. Some molecular sieves were added and the reaction mixture was refluxed for 5 hours. After cooling, the reaction mixture was evaporated in vacuo to dryness, dissolved in $CH_2Cl_2$ and washed with sat. sol. NaCl, 20% citric acid, sat. sol. NaCl. The organic layer was dried over $Na_2SO_4$ and evaporated in vacuo to dryness. The crude product was purified by flash column chromatography on 230–400 mesh silica gel, eluting with a mixture of i-$Pr_2O$/EtOAc 70:30 containing 0.5% of 85% formic acid, and then triturated with i-$Pr_2O$ to yield 2.0 g of the title compound.

$C_{31}H_{29}N_3O_5$
M.P.=158–162° C.
M.W.=523.59
$[\alpha]_D^{20}=-38.6$ (c=0.5, MeOH)
Elemental analysis: Calcd. C, 71.11; H, 5.58; N, 8.03; Found C, 70.90; H, 5.56; N, 7.95
I.R.(KBr): 3280; 3150-3000; 1710; 1640-1620 $cm^{-1}$.
300 MHz $^1H$ NMR (DMSO-$d_6$) δ 14.80 (s br, 1H); 9.30 (d, 1H); 9.08 (t br, 1H); 8.07 (d, 1H); 7.94(dd, 2H); 7.79-7.70 (m, 1H); 7.60 (m, 2H); 7.52-7.38 (m, 7H); 7.29 (dd, 1H); 6.32 (d, 1H); 6.27 (d, 1H); 5.07 (dt, 1H); 3.76-3.64 (m, 2H); 3.28-3.00 (m, 2H); 1.90-1.74 (m, 2H); 1.00 (t, 3H).
MS (EI; TSQ 700; source 180 C;70 V; 200 uA): 425; 407.

EXAMPLE 14

(S)-N-(a-ethylbenzyl)-3-[2-(3-carboxypropanoyl) aminoethoxy]-2-phenylquinoline-4-carboxamide 2.0 g (4.7 mmol) of (S)-N-(α-ethylbenzyl)-3-(2-aminoethoxy)-2-phenylquinoline-4-carboxamide (compound of Description 4) and 0.6 g (6.2 mmol) of succinic anhydride were dissolved in 50 ml of toluene; some triturated molecular sieves were added and the reaction mixture was refluxed in a Dean Stark apparatus for 4 hours. The reaction mixture was evaporated in vacuo to dryness, dissolved in 100 ml of $CH_2Cl_2$ and washed with sat. sol. NaCl, 20% citric acid and sat. sol. NaCl. The organic layer was dried over $Na_2SO_4$ and evaporated in vacuo to dryness to yield 2.3 g of the crude product which was purified by flash column chromatography on 230–400 mesh silica gel, eluting initially with a mixture of $CH_2Cl_2$/MeOH 9:1 and then with a mixture of $CH_2Cl_2$/MeOH 8:2. The crude solid obtained was triturated with i-$Pr_2O$/i-PrOH, washed and dried to yield 1.4 g of the title compound.

$C_{31}H_{31}N_3O_5$
M.P.=118–122° C.
M.W.=525.60
$[\alpha]_D^{20}=-32.1$ (c=0.5, MeOH)
I.R.(KBr): 3600-3120; 3100-3000; 1740-1700; 1680-1600 $cm^{-1}$.
300 MHz $^1H$ NMR (DMSO-$d_6$) δ 11.98 (s br, 1H); 9.28 (d, 1H); 8.07 (d, 1H); 7.99 (dd, 2H); 7.73(ddd, 1H); 7.66 (t br, 1H); 7.61-7.48 (m, 5H); 7.46 (d, 2H); 7.39 (dd, 2H); 7.30 (dd, 1H); 5.05 (dt, 1H); 3.69-3.57 (m, 2H); 3.12-2.91 (m, 2H); 2.34 (m, 2H); 2.21 (m, 2H); 1.90-1.75 (m, 2H); 1.00 (t, 3H).
MS (FAB POS; thioglycerine matrix; FAB gas Xe; 8 kV; source 50 ): 526 (MH+); 383; 291.

EXAMPLE 15

(S)-N-(a-ethylbenzyl)-3-[2-(N-methyl-8-azabicyclo [3.2.1]oct-3-yl)aminoethoxy]-2-phenylquinoline-4-carboxamide hydrochloride 1.50 g (3.53 mmol) of (S)-N-(α-ethylbenzyl)-3-(2-aminoethoxy)-2-phenylquinoline-4-carboxamide (compound of Description 4) and 0.98 g (7.06 mmol) of tropinone were dissolved in 30 ml MeOH and 100 ml toluene; 0.22 (3.53 mmol) of $NaCNBH_3$ were added portionwise and the reaction mixture was refluxed for 24 hours in a Dean-Stark apparatus. The reaction was quenched with 5 ml of 2N NaOH and, after stirring at room temperature for 20 minutes, was evaporated in vacuo to dryness. The residue was dissolved in 20% citric acid and extracted twice with EtOAc; the aqueous layer was basified with solid $K_2CO_3$ and extracted with $CH_2Cl_2$. The organic layer was dried over $Na_2SO_4$ and evaporated in vacuo to dryness, to afford 1.8 g of a yellow solid which was flash chromatographed on 230–400 mesh silica gel, eluting with a mixture of EtOAc/MeOH 80:20 containing 2% of 28% $NH_4OH$. The crude product (0.17 g) was dissolved in MeOH and the solution acidified with HCl/$Et_2O$ to yield the corresponding hydrochloride, which was recrystallized from EtOAc/abs. EtOH to obtain 0.10 g of the title compound as a slightly brown powder.

$C_{35}H_{40}N_4O_2$.HCl
M.P.=200–203° C.
M.W.=585.19
I.R.(KBr): 3403; 2966-2760; 1637; 1558 $cm^{-1}$.
300 MHz $^1H$ NMR (DMSO-$d_6$) δ 9.29 and 9.26 (d, 1H); 8.05 (d, 1H); 7.92 (dd, 2H); 7.71 (ddd, 1H); 7.61-7.50 (m, 5H); 7.45 (d, 2H); 7.38 (dd, 2H); 7.28 (dd, 1H); 5.09 (dt, 1H); 3.70-3.60 (m, 2H); 3.32 (m, 2H); 2.95 (m, 1H); 2.82 (m, 1H); 2.41 (t, 2H); 2.11 and 2.08 (s, 3H); 1.90-1.65 (m, 6H); 1.41-1.31 (m, 2H); 1.23–1.03 (m, 2H); 0.98 (t, 3H).
MS (EI; TSQ 700; source 180 C;70 V; 200 uA): 548(M+); 386; 305; 166; 124; 82.

EXAMPLE 16

(S)-N-(a-ethylbenzyl)-3-[2-(2'-carboxybenzoyl) aminoethoxy]-2-phenylquinoline-4-carboxamide 0.85 g (2.0 mmol) of (S)-N-(a-ethylbenzyl)-3-[2-(2'-methoxycarbonylbenzoyl)amino ethoxy]-2-phenylquinoline-4-carboxamide (compound of Example 17) were dissolved in 25 ml of 10% NaOH and 5 ml of 1,4-dioxane. The solution was warmed to 60° C. for 15 minutes, then it was extracted with $CH_2Cl_2$, washed with 10% citric acid and sat. sol. NaCl, dried over $Na_2SO_4$ and evaporated in vacuo to dryness. The residue was purified by gradient flash column chromatography on 230–400 mesh silica gel utilising a mixture of i-$Pr_2O$/EtOAc/HCOOH (85%)/$H_2O$ 70:30:0.5:0.5 as starting eluent and a mixture of i-$Pr_2O$/EtOAc/HCOOH (85%)/$H_2O$ 60:40:0.5:0.5 as final eluent. The crude product so obtained was triturated with i-$Pr_2O$/i-PrOH to yield 0.2 g of the title compound.

$C_{35}H_{31}N_3O_5$
M.P.=96–115° C.

M.W.=573.65

[α]$_D^{20}$=−33.3 (c=0.5, MeOH)

I.R.(KBr): 3400; 3257; 3100-3000; 1723; 1637; 1581 cm$^{-1}$.

300 MHz $^1$H NMR (DMSO-d$_6$) δ 12.75 (s br, 1H); 9.31 (d, 1H); 8.07 (d, 1H); 8.00 (m, 3H); 7.76-7.69(m, 2H); 7.57 (m, 2H); 7.55-7.37 (m, 9H); 7.29 (dd, 1H); 7.18 (m, 1H); 5.06 (dt, 1H); 3.79 (t, 2H); 3.34-3.15 (m, 2H); 1.90-1.75 (m, 2H); 0.97 (t, 3H);.

MS (EI; TSQ 700; source 180 C;70 V; 200 uA): 555; 526; 422; 382; 262; 247; 219; 174; 119.91.

EXAMPLE 17

(S)-N-(a-ethylbenzyl)-3-[2-(2'methoxycarbonylbenzoyl)aminoethoxy]-2-phenylquinoline-4-carboxamide 2.4 g (5.7 mmol) of (S)-N-(α-ethylbenzyl)-3-(2-aminoethoxy)-2-phenylquinoline-4-carboxamide (compound of Description 4) were dissolved, under nitrogen atmosphere, in 50 ml of dry CH$_2$Cl$_2$; 0.88 ml (6.2 mmol) of TEA were added and the solution was cooled to 0° C. 1.1 g (5.8 mmol) of methyl 2-chlorocarbonylbenzoate (obtained by treating the corresponding mono acid mono ester with oxalyl chloride), dissolved in 50 ml of CH$_2$Cl$_2$, were added dropwise at 0° C. and the solution was stirred at room temperature for 4 hours. The reaction mixture was washed with H$_2$O, 20% citric acid, sat. sol. NaHCO$_3$, sat. sol. NaCl, dried over Na$_2$SO$_4$ and evaporated in vacuo to dryness. 1.0 g of the residue was purified by flash column chromatography in vacuo to dryness. 1.0 g of the residue were purified by flash column chromatography on 230–400 mesh silica gel, eluting with a mixture of hexane/EtOAc 1:1, and then triturated with i-Pr$_2$O to yield 0.9 g of the title compound.

C$_{36}$H$_{33}$N$_3$O$_5$

M.P.=133–135° C.

M.W.=587.68

[α]$_D^{20}$=−35.6 (c=0.5, MeOH)

Elemental analysis: Calcd. C, 73.22; H, 5.20; N, 6.57; Found C, 73.30; H, 5.61; N, 7.08.

I.R.(KBr): 3500-3120; 3100-3000; 1730; 1660-1620 cm$^{-1}$.

300 MHz $^1$H NMR (DMSO-d$_6$) δ 9.30 (d, 1H); 8.10 (t, 1H); 8.08 (d, 1H); 8.01 (d, 2H); 7.70-7.68(m, 2H); 7.59-7.38 (m, 11H); 7.30 (m, 2H); 5.06 (dt, 1H); 3.79 (t, 2H); 3.61 (s, 3H); 3.30-3.13 (m, 2H); 1.90-1.75 (m, 2H); 0.95 (t, 3H).

MS (EI; TSQ 700; source 180 C;70 V; 200 uA): 422; 382; 264; 247; 219; 206; 174; 163; 147.

EXAMPLE 18

(S,E)-N-(a-ethylbenzyl)-3-[2-(3-methoxycarbonylpropenoyl)aminoethoxy]-2-phenylquinoline-4-carboxamide 1.4 g (3.3 mmol) of (S)-N-(α-ethylbenzyl)-3-(2-aminoethoxy)-2-phenylquinoline-4-carboxamide (compound of Description 4) were dissolved, under nitrogen atmosphere, in 35 ml of dry CH$_2$Cl$_2$; 0.77 ml (5.5 mmol) of TEA were added, the solution was cooled to 0° C. and 0.4 g (3.4 mmol) of methyl 3-chlorocarbonylpropenoate (compound of Description 5), dissolved in 25 ml of CH$_2$Cl$_2$, were added dropwise. The reaction was stirred at room temperature for 2 days, washed with H$_2$O, 20% citric acid, sat. sol. NaHCO$_3$, sat. sol. NaCl, dried over Na$_2$SO$_4$ and evaporated in vacuo to dryness. The residue was purified by gradient flash column chromatography on 230–400 mesh silica utilising a mixture of hexane/EtOAc 8:2 as starting eluent and a mixture of hexane/EtOAc 3:7 as final eluent. The crude product so obtained was further purified by preparative HPLC to yield 0.30 g of the title compound.

C$_{32}$H$_{31}$N$_3$O$_5$

M.P.=122–125° C.

M.W.=537.62

[α]$_D^{20}$=−37.7 (c=0.5, MeOH)

Elemental analysis: Calcd. C, 71.49; H, 5.81; N, 7.82; Found C, 71.19; H, 5.68; N, 7.77.

I.R.(KBr): 3500-3120; 3100-3000; 1730; 1670-1620; 1550 cm$^{-1}$.

300 MHz $^1$H NMR (DMSO-d$_6$) δ 9.30 (d, 1H); 8.47 (t br, 1H); 8.06 (d, 1H); 7.97 (dd, 2H); 7.73 (ddd, 1H); 7.60 (m, 2H); 7.50-7.37 (m, 7H); 7.29 (dd, 1H); 6.95 (d, 1H); 6.51 (d, 1H); 5.07 (dt, 1H); 3.75 (s, 3H); 3.69 (m, 2H); 3.25-3.00 (m, 2H); 1.90-1.75 (m, 2H); 0.97 (t, 3H).

MS (EI; TSQ 700; source 180 C;70 V; 200 uA): 537 (M+); 507; 404; 382; 301; 249; 156.

EXAMPLE 19

(S,Z)-N-(a-ethylbenzyl)-3-[2-(3-methoxycarbonylpropenoyl)aminoethoxy]-2-phenylquinoline-4-carboxamide By continuing the elution of the flash column chromatography of Example 18, 0.31 g of the title compound were isolated.

C$_{32}$H$_{31}$N$_3$O$_5$

M.P.=80–90° C.

M.W.=537.62

[α]$_D^{20}$=−37.2 (c=0.5, MeOH)

Elemental analysis: Calcd. C, 71.49; H, 5.81; N, 7.82; Found C, 71.05; H, 5.93; N, 7.68.

I.R.(KBr): 3500-3120; 3100-3000; 1730; 1670-1620; 1550 cm$^{-1}$.

300 MHz $^1$H NMR (DMSO-d$_6$) δ 9.31 (d, 1H); 8.07 (d, 1H); 8.05 (t br, 1H); 7.98 (dd, 2H); 7.73 (ddd, 1H); 7.59 (m, 2H); 7.55-7.38 (m, 7H); 7.29 (dd, 1H); 6.22 (Abq, 2H); 5.09 (dt, 1H); 3.66 (m, 2H); 3.58 (s, 3H); 3.20-2.95 (m, 2H); 1.83 (m, 2H); 0.90 (t, 3H).

MS (EI; TSQ 700; source 180 C;70 V; 200 uA): 537 (M+); 476; 371; 247; 156; 124.

EXAMPLE 20

(S,E)-N-(a-ethylbenzyl)-3-[2-(3-carboxypropenoyl) aminoethoxy]-2-phenylquinoline-4-carboxamide 0.2 g (0.4 mmol) of (S,E)-N-(a-ethylbenzyl)-3-[2-(3-methoxycarbonylpropenoyl) aminoethoxy]-2-phenylquinoline-4-carboxamide (compound of Example 18) were dissolved in 25 ml of 10% NaOH and 5 ml of 1,4-dioxane and warmed to 60° C. for 15 minutes. After cooling, the reaction mixture was extracted with CH$_2$Cl$_2$ and washed with 10% citric acid and sat. sol. NaCl. The organic layer was dried over Na$_2$SO$_4$, evaporated in vacuo to dryness and triturated with i-Pr$_2$O to yield 83 mg of the title compound.

C$_{31}$H$_{29}$N$_3$O$_5$

M.P.=230–233° C.

M.W.=523.59

$[\alpha]_D^{20}$=−39.6 (c=0.5, MeOH)

I.R.(KBr): 3500-3120; 3100-3000; 1740-1700; 1680-1600; 1550-1520 cm$^{-1}$.

300 MHz $^1$H NMR (DMSO-d$_6$) δ 9.30 (d, 1H); 8.42 (t br, 1H); 8.06 (d, 1H); 7.97 (dd, 2H); 7.73 (ddd, 1H); 7.59 (m, 2H); 7.50-7.37 (m, 7H); 7.29 (dd, 1H); 6.88 (d, 1H); 6.45 (d, 1H); 5.09 (dt, 1H); 3.68 (m, 2H); 3.24-2.99 (m, 2H); 1.80 (m, 2H); 0.96 (t, 3H).

MS (EI; TSQ 700; source 180 C;70 V; 200 uA): 523 (M+); 382; 264; 247; 219; 119; 91.

EXAMPLE 21

(S)-N-(a-ethylbenzyl)-3-(cyanomethoxy)-2-phenylquinoline-4-carboxamide 2.0 g (5.23 mmol) of (S)-N-(α-ethylbenzyl)-3-hydroxy-2-phenylquinoline-4-carboxamide (compound of Description 1), 2.21 g of K$_2$CO$_3$, 0.26 g (1.57 mmol) of KI and 0.52 ml (7.85 mmol) of bromoacetonitrile were stirred in 30 ml of dry THF for 5 hours. The inorganic salts were filtered off and the filtrate was evaporated in vacuo to dryness. The residue was dissolved in CH$_2$Cl$_2$ and the organic phase was washed with H$_2$O, sat. sol. NaHCO$_3$, sat. sol. NaCl, separated, dried over Na$_2$SO$_4$ and evaporated in vacuo to dryness to afford 2.10 g of a brown oil which was flash chromatographed on 230–400 mesh silica gel, eluting with a mixture of hexane/EtOAc 70:30. The crude product was triturated with hexane, filtered, washed and dried to yield 0.75 g of the title compound as a white solid.

C$_{27}$H$_{23}$N$_3$O$_2$

M.P.=70–72° C.

M.W.=421.50

$[\alpha]_D^{20}$=−40.4 (c=1, MeOH)

I.R.(KBr): 3413; 3264; 3053; 2943; 1645; 1529 cm$^{-1}$.

300 MHz $^1$H NMR (DMSO-d$_6$) δ 9.37 (d, 1H); 8.11 (d, 1H); 7.95 (dd, 2H); 7.80 (ddd, 1H); 7.67-7.55(m, 5H); 7.45-7.38 (m, 4H); 7.20 (dd, 1H); 5.10 (dt, 1H); 4.60 (Abq, 2H); 1.85 (dq, 2H); 1.00 (t, 3H).

MS (EI; TSQ 700; source 180 C;70 V; 200 uA): 421 (m+); 392; 381; 287; 247; 219; 190; 134.

EXAMPLE 22

(S)-N-(a-ethylbenzyl)-3-(2-phenylquinoline-4-carboxamide 1.0 g (2.3 mmol) of (S)-N-(α-ethylbenzyl)-3-(2-aminoethoxy)-2-phenylquinoline-4-carboxamide (compound of Description 4) were dissolved in 20 ml of dry CH$_2$Cl$_2$; 0.37 ml (2.6 mmol) of TEA were added and the reaction mixture was cooled to 0° C. 0.4 g (2.6 mmol) of phenylacetyl chloride, dissolved in 20 ml of CH$_2$Cl$_2$, were added dropwise and the reaction mixture was stirred at room temperature for 4 hours and then washed with 20% citric acid, sat. sol. NaHCO$_3$ and brine. The organic layer was dried over Na$_2$SO$_4$, evaporated in vacuo to dryness and triturated with i-Pr$_2$O to yield 0.9 g of the title compound.

C$_{35}$H$_{33}$N$_3$O$_3$

M.P.=95–105° C.

M.W.=543.66

$[\alpha]_D^{20}$=−32.6 (c=0.5, MeOH)

Elemental analysis: Calcd. C, 77.32; H, 6.12; N, 7.73; Found C, 76.89; H, 6.19; N, 7.61.

I.R.(KBr): 3400-3100; 3100-3000; 1650-1620 cm$^{-1}$.

300 MHz $^1$H NMR (DMSO-d$_6$) δ 9.30 (d, 1H); 8.06 (d, 1H); 7.98 (m, 2H); 7.86 (t br, 1H); 7.72 (ddd, 1H); 7.59 (m, 2H); 7.51 (m, 3H); 7.45 (d, 2H); 7.39 (dd, 2H); 7.30-7.12 (m, 6H); 5.09 (dt, 1H); 3.62 (m, 2H); 3.29 (s, 2H); 3.12-2.91 (m, 2H); 1.90-1.75 (m, 2H); 0.98 (t, 3H).

MS (EI; TSQ 700; source 180 C;70 V; 200 uA): 543 (M+); 410; 382; 162.

EXAMPLE 23

(S)-N-(a-ethylbenzyl)-3-[2-((S)-a-aminophenylacetyl)aminoethoxy]-2-phenylquinoline-4-carboxamide The reaction to obtain the FMOC-protected title compound was conducted as described in Example 25, starting from 2.8 g (6.7 mmol) of (S)-N-(α-ethylbenzyl)-3-(2-aminoethoxy)-2-phenylquinoline-4-carboxamide (compound of Description 4), 1.1 ml (8.0 mmol) of TEA and 3.1 g (8.0 mmol) of (S)-FMOC-phenylglycinyl chloride. The reaction was stirred at room temperature for 20 hours and worked up as described in Example 25 to yield 4.5 g of the FMOC protected title compound, which was deprotected by stirring at room temperature for 30 minutes with 90 ml of a 10% solution of diethylamine in DMF. The reaction mixture was then evaporated in vacuo and purified by gradient flash column chromatography on 230–400 mesh silica gel utilising EtOAc as starting eluent and a mixture of EtOAc/MeOH 9:1 as final eluent, to yield, after trituration with i-Pr$_2$O, 1.4 g of the title compound.

C$_{35}$H$_{34}$N$_4$O$_3$

M.P.=140–145° C.

M.W.=558.68

$[\alpha]_D^{20}$=−17.0 (c=0.5, MeOH)

Elemental analysis: Calcd. C, 75.25; H, 6.13; N, 10.03; Found C, 72.70; H, 6.11; N, 9.80.

I.R. (KBr): 3440-3110; 3100-3000; 1650-1630; 1585 cm$^{-1}$.

300 MHz $^1$H-NMR (DMSO-d$_6$): δ 9.30 (d, 1H); 8.08 (d, 1H); 7.97 (dd, 2H); 7.92 (t br, 1H); 7.72 (dd, 1H); 7.60-7.48 (m, 5H); 7.45 (d, 2H); 7.38 (dd, 2H); 7.30-7.20 (m, 6H); 5.09 (dt, 1H); 4.21 (s, 1H); 3.65 (t, 2H); 3.07 (dt, 2H); 2.10 (s br, 2H); 1.90-1.75 (m, 2H); 0.95 (t, 3H).

MS (EI; TSQ 700; source 180 C; 70 V; 200 uA); 541; 453; 382; 292; 291; 247; 219; 106.

EXAMPLE 24

(S)-N-(a-ethylbenzyl)-3-[2-((R)-a-aminophenylacetyl)aminoethoxy]-2-phenylquinoline-4-carboxamide The reaction was conducted exactly as described in Example 23, utilising the (R)-FMOC-phenylglycinyl chloride instead of the (S). The same amounts of all the reagents were used. 0.8 g of the title compound were obtained.

C$_{35}$H$_{34}$N$_4$O$_3$

M.P.=92–94° C.

M.W.=558.68

$[\alpha]_D^{20}$=−52.8 (c=0.5, MeOH)

Elemental analysis: Calcd. C, 75.25; H, 6.13; N, 10.03; Found C, 74.15; H, 6.19; N, 9.91.

I.R. (KBr): 3440-3110; 3100-3000; 1670-1630 cm$^{-1}$.

300 MHz $^1$H-NMR (DMSO-d$_6$): δ 9.30(d, 1H); 8.07 (d, 1H); 7.96 (d, 2H); 7.90 (t br, 1H); 7.72 (m, 1H); 7.60-7.50

(m, 5H); 7.44 (d, 2H); 7.38 (dd, 2H); 7.29-7.19 (m, 6H); 5.09 (dt, 1H); 4.20 (s, 1H); 3.60 (m, 2H); 3.16-2.91 (m, 2H); 2.11 (s br, 2H); 1.90-1.75 (m, 2H); 0.96 (t, 3H).

MS (EI; TSQ 700; source 180 C; 70 V; 200 uA): 541; 453; 382; 292; 291; 247; 219; 106.

EXAMPLE 25

(S)-N-(a-ethylbenzyl)-3-(2-aminoacetylaminoethoxy)-2-phenylquinoline-4-carboxamide 3.0 g (7.1 mmol) of (S)-N-(α-ethylbenzyl)-3-(2-aminoethoxy)-2-phenylquinoline-4-carboxamide (compound of Description 4) were dissolved, under nitrogen atmosphere, in 60 ml of $CH_2Cl_2$ and 1.2 ml (8.5 mmol) of TEA were added; the solution was cooled to 0° C. and 2.7 g (8.5 mmol) of (9-fluorenylmethoxy carbonyl)glycinyl chloride (FMOC-glycinyl chloride), dissolved in 60 ml of $CH_2Cl_2$, were added dropwise. The reaction mixture was stirred at room temperature for 3 hours and then washed with sat. sol. NaCl, 20% citric acid, sat. sol. $NaHCO_3$, sat. sol. NaCl, dried over $Na_2SO_4$ and evaporated in vacuo to dryness. The crude product was purified by gradient flash column chromatography on 230–400 mesh silica gel, utilising a mixture of hexane/EtOAc 1:1 as starting eluent and a mixture of EtOAc/MeOH 9:1 as final eluent. The product (5.0 g) was dissolved in 100 ml of a 10% solution of diethylamine in DMF and stirred at room temperature for 30 minutes. The reaction mixture was then evaporated in vacuo and purified by gradient flash column chromatography on 230–400 mesh silica gel, utilising a mixture of EtOAc/MeOH 9:1 as starting eluent and a mixture of EtOAc/MeOH 7:3 as final eluent, to yield 0.6 g of the title compound.

$C_{29}H_{30}N_4O_3$

M.P.=55–60° C. dec.

M.W.=482.58

$[\alpha]_D^{20}$=−33.7 (c=0.5, MeOH)

Elemental analysis: Calcd. C, 72.12; H, 6.27; N, 11.61; Found C, 70.12; H, 6.45; N, 10.81.

I.R. (KBr): 3500-3110; 3100-3000; 1680-1650; 1638 cm$^{-1}$.

300 MHz $^1$H-NMR (DMSO-d$_6$); δ 9.29 (d, 1H); 8.06 (d, 1H); 7.98 (dd, 2H); 7.74 (ddd, 1H); 7.68 (t, br, 1H); 7.60-7.38 (m, 9H); 7.30 (dd, 1H); 5.09 (dt, 1H); 3.70-3.55 (m, 2H); 3.18-3.00 (m, 2H); 2.99 (s, 2H); 1.90-1.78 (m, 2H); 1.00 (t, 3H).

MS (EI; TSQ 700; source 180 C; 70 V; 200 uA); 482 (M+); 382; 291; 264; 247; 219; 190; 141; 119; 101; 91.

EXAMPLE 26

(S)-N-(a-ethylbenzyl)-3-[2-(4-pyridylacetyl)aminoethoxy]-2-phenylquinoline-4-carboxamide 0.41 g (2.4 mmol) of 4-pyridylacetic acid hydrochloride were suspended in 80 ml of $CH_2Cl_2$; the suspension was cooled to 0° C. and 0.33 ml (2.4 mmol) of TEA, 0.64 g (4.7 mmol) of HOBT and 1.0 g (2.4 mmol) of (S)-N-(α-ethylbenzyl)-3-(2-aminoethoxy)-2-phenylquinoline-4-carboxamide (compound of Description 4) were added. 0.58 g (2.8 mmol) of DCC, dissolved in 10 ml of $CH_2Cl_2$, were added dropwise and the reaction mixture was stirred at 0° C. for 1 h and at room temperature overnight. The precipitated dicyclohexylurea was filtered off and the filtrate was washed with 20% citric acid, sat. sol. NaCl and brine, dried over $Na_2SO_4$ and evaporated in vacuo to dryness. The crude product was purified by flash column chromatography on 230–400 mesh silica gel, eluting with a mixture of $CH_2Cl_2$/MeOH 95:5 containing 0.5% $NH_4OH$ (28%), to yield, after trituration with i-Pr$_2$O, 0.85 g of the title compound.

$C_{34}H_{32}N_4O_3$

M.P.=76° C. dec.

M.W.=544.65

$[\alpha]_D^{20}$=−28.6 (c=0.5, MeOH)

Elemental analysis: Calcd. C, 74.98; H, 5.92; N, 10.29; Found C, 74.21; H, 5.95; N, 10.17.

I.R. (KBr): 3269; 3100-3000; 1646; 1603 cm$^{-1}$.

300 MHz $^1$H-NMR (DMSO-d$_6$); δ 9.30 (d, 1H); 8.41 (d, 2H); 8.08 (d, 1H); 8.00 (m, 3H); 7.74 (ddd, 1H); 7.62-7.48 (m, 5H); 7.45 (d, 2H); 7.40 (dd, 2H); 7.28 (dd, 1H); 7.18 (d, 2H); 5.10 (dt, 1H); 3.63 (m, 2H); 3.34 (s, 2H); 3.14-2.92 (m, 2H); 1.80 (m, 2H); 0.98 (t, 3H).

MS (EI; TSQ 700; source 180 C; 70 V; 200 uA): 544 (M+); 411; 382; 163.

EXAMPLE 27

(S)-N-(a-ethylbenzyl)-3-[2-(3-pyridylacetyl)aminoethoxy]-2-phenylquinoline-4-carboxamide Prepared as described in Example 26 from 0.41 g (2.4 mmol) of 3-pyridylacetic acid hydrochloride, 1.0 g (2.4 mmol) of (S)-N-(α-ethylbenzyl)-3-(2-aminoethoxy)-2-phenylquinoline-4-carboxamide (compound of Description 4), 0.33 ml (2.4 mmol) of TEA, 0.64 g (4.7 mmol) of HOBT and 0.58 g (2.8 mmol) of DCC. The work up and the purification of the reaction mixture were conducted as described in Example 26. After trituration with i-Pr$_2$O, 0.76 g of the title compound were obtained.

$C_{34}H_{32}N_4O_3$

M.P.=89° C. dec.

M.W.=544.65

$[\alpha]_D^{20}$=−31.7 (c=0.5, MeOH)

Elemental analysis: Calcd. C, 74.98; H, 5.92; N, 10.29; Found C, 74.14; H, 6.00; N, 10.17.

I.R. (KBR): 3275; 3100-3000; 1643; 1548 cm$^{-1}$.

300 MHz $^1$H-NMR (DMSO-d$_6$): δ 9.29 (d,1H); 8.40 (m, 2H); 8.06 (d, 1H); 7.98 (m, 3H); 7.72 (ddd, 1H); 7.60-7.48 (m, 6H); 7.45 (d, 2H); 7.39 (dd, 2H); 7.29 (m, 2H); 5.08 (dt, 1H); 3.65 (m, 2H); 3.33 (s, 2H); 3.13-2.91 (m, 2H); 2.90-1.75 (m, 2H); 1.00 (t, 3H).

MS (EI; TSQ 700; source 180 C; 70 V; 200 uA): 544 (M+); 515; 411; 382; 353; 264; 247; 163.

EXAMPLE 28

(S)-N-(a-ethylbenzyl)-3-[2-(2-pyridylacetyl)aminoethoxy]-2-phenylquinoline-4-carboxamide Prepared as described in Example 26 from 0.41 g (2.4 mmol) of 2-pyridylacetic acid hydrochloride, 1.0 g (2.4 mmol) of (S)-N-(α-ethylbenzyl)-3-(2-aminoethoxy)-2-phenylquinoline-4-carboxamide (compound of Description 4), 0.33 ml (2.4 mmol) of TEA, 0.64 g (4.7 mmol) of HOBT and 0.58 g (2.8 mmol) of DCC. The work up and the purification of the reaction mixture were conducted as described in Example 26. After trituration with i-Pr$_2$O, 0.10 g of the title compound were obtained.

$C_{34}H_{32}N_4O_3$

M.P.=74° C. dec.

M.W.=544.65

[α]$_D^{20}$=−34.1 (c=0.5, MeOH)

I.R. (KBr): 3269; 3100-3000; 1645; 1592; 1540 cm$^{-1}$.

300 MHz $^1$H-NMR (DMSO-d$_6$): δ 9.28 (d, 1H); 8.44 (d, 1H); 8.08-7.90 (m, 4H); 7.75-7.65 (m, 2H); 7.60-7.37 (m, 9H); 7.30-7.20 (m, 3H); 5.10 (dt, 1H); 3.62 (m, 2H); 3.50 (s, 2H); 3.12-2.95 (m, 2H); 1.80 (m, 2H); 0.98 (t, 3H).

MS (EI; TSQ 700; source 180 C; 70 V; 200 uA): 514; 452; 382; 247; 163.

EXAMPLE 29

(S)-N-(a-ethylbenzyl)-3-[2-(2'-carboxyphenylacetyl) aminoethoxy]-2-phenylquinoline-4-carboxamide 1.0 g (2.4 mmol) of (S)-N-(α-ethylbenzyl)-3-(2-aminoethoxy)-2-phenylquinoline-4-carboxamide (compound of Description 4) were dissolved in 10 ml of toluene; 0.51 g (2.8 mmol) of homophthalic acid were added and the reaction mixture was refluxed for 3.5 hours. After cooling, the solvent was evaporated in vacuo to dryness and the residue was dissolved in CH$_2$Cl$_2$ and washed with brine. The organic layer was dried over Na$_2$SO$_4$ and evaporated in vacuo to dryness. The residue was purified by gradient flash column chromatography on 230–400 mesh silica gel, utilising a mixture of hexane/EtOAc 7:3 containing 0.5% NH$_4$OH (28%) as starting eluent and a mixture of EtOAc/MeOH 8:2 containing 2% NH$_4$OH (28%) as final eluent, to yield 0.89 g of a mixture of the title compound and of (S)-N-(a-ethylbenzyl)-3-[2-(2'-carboxymethylbenzoyl) aminoethoxy]-2-phenylquinoline-4-carboxamide (compound of Example 30). 0.4 g of this mixture were purified by preparative HPLC to yield 0.17 g of the title compound.

C$_{36}$H$_{33}$N$_3$O$_5$

M.P.=108° C. dec.

M.W.=587.67

[α]$_D^{20}$=−28.3 (c=0.5, MeOH)

I.R. (KBr): 3247; 3100-3000; 1710-1650; 1635; 1547 cm$^{-1}$.

300 MHz $^1$H-NMR (DMSO-d$_6$): δ 12.80 (s br, 1H); 9.29 (d, 1H); 8.08 (d, 1H); 7.99 (d, 2H); 7.79 (d, 1H); 7.75 (t br, 1H); 7.72 (ddd, 1H); 7.60-7.50 (m, 5H); 7.48-7.15 (m, 7H); 7.17 (d, 1H); 5.09 (dt, 1H); 3.72 (s, 2H); 3.65 (m, 2H); 3.12-2.92 (m, 2H); 1.81 (m, 2H); 0.90 (t, 3H).

MS (EI; TSQ 700; source 180 C; 70 V; 200 uA): 569; 425; 407; 396; 383; 291; 277; 262; 247; 219; 188; 165; 118; 91.

EXAMPLE 30

(S)-N-(a-ethylbenzyl)-3-[2-(2'-carboxymethylbenzoyl)aminoethoxy]-2-phenylquinoline-4-carboxamide By continuing the preparative HPLC of Example 29, 0.063 g of the title compound were obtained.

C$_{36}$H$_{33}$N$_3$O$_5$

M.P.=83° C. dec.

M.W.=587.67

[α]$_D^{20}$=−33.5 (c=0.5, MeOH)

I.R. (KBr): 3273; 3100-3000; 1733; 1641; 1612; 1594; 1538 cm$^{-1}$.

300 MHz $^1$H-NMR (DMSO-d$_6$): δ 12.20 (s br, 1H); 9.31 (d, 1H); 8.30 (s br, 1H); 8.06 (d, 1H); 7.99 (m, 2H); 7.72 (ddd, 1H); 7.57 (m, 2H); 7.48-7.38 (m, 8H); 7.30-7.20 (m, 4H); 5.04 (dt, 1H); 3.79 (t, 2H); 3.63 (s, 2H); 3.32-3.15 (m, 2H); 1.88-1.75 (m, 2H); 0.94 (t, 3H).

MS (EI; TSQ 700; source 180 C; 70 V; 200 uA): 569; 425; 407; 396; 383; 291; 277; 262; 247; 219; 188; 165; 118; 91.

EXAMPLE 31

(S)-N-(a-ethylbenzyl)-3-(2-benzylaminoethoxy)-2-phenylquinoline-4-carboxamide hydrochloride 1.5 g (3.52 mmol) of (S)-N-(α-ethylbenzyl)-3-(2-aminoethoxy)-2-phenylquinoline-4-carboxamide (compound of Description 4) and 0.71 ml (7.04 mmol) of benzaldehyde were dissolved in 40 ml of MeOH; after cooling to 10° C., 2.21 g (3.52 mmol) of NaCHBH$_3$ were added portionwise, under nitrogen atmosphere, and the reaction stirred at room temperature overnight. The reaction was quenched with 50 ml of 2N NaOH and extracted with ether; the organic layer was separated, dried over Na$_2$SO$_4$ and evaporated in vacuo to dryness. The crude product was purified by 230–400 mesh silica gel gradient column chromatography, eluting with hexane/EtOAc (from 20 to 30%). The crude product (0.64 g) was dissolved in MeOH and the solution acidified with HCl/Et$_2$O to yield the corresponding hydrochloride, which was recrystallized from i-Pr$_2$O/i-PrOH to obtain 0.50 g of the title compound as a pale yellow powder.

C$_{34}$H$_{33}$N$_3$O$_2$.HCl

M.P.=165–169° C.

M.W.=552.110

[α]$_D^{20}$=−27.7 (c=1.1, MeOH)

I.R. (KBr): 3498; 3185; 2968-2637; 1650; 1535 cm$^{-1}$.

300 MHz $^1$H-NMR 353 K (DMSO-d$_6$): δ 8.89 (d, 1H); 8.01 (d, 1H); 7.74 (m, 2H); 7.62 (dd, 2H); 7.57-7.44 (m, 6H); 7.39 (dd, 2H); 7.29 (dd, 1H); 7.20-7.10 (m, 3H); 6.89 (m, 2H); 5.13 (dt, 1H); 3.70 (s, 2H); 3.10 (s, 2H); 2.02-1.80 (m, 2H); 1.68 (s, 3H); 0.98 (t, 3H).

MS (EI, TSQ 700, source °180 C., 70 V, 200 uA): 408; 273; 380.

EXAMPLE 32

(S)-N-(a-ethylbenzyl)-3-(2-dibenzylaminoethoxy)-2-phenylquinoline-4-carboxamide hydrochloride By continuing the elution of the chromatographic column of Example 31, 0.40 g of the crude title compound were obtained. This product was dissolved in MeOH and the solution acidified with HCl/Et$_2$O to yield the corresponding hydrochloride, which was recrystallized from Et$_2$O/MeOH to obtain 0.26 g of the title compound.

C$_{41}$H$_{39}$N$_3$O$_2$.HCl

M.P.=144–145° C.

M.W.=642.28

[α]$_D^{20}$=−25.3 (c=0.25, MeOH)

I.R. (KBr): 3419; 3163; 3059-2933; 1656; 1542 cm$^{-1}$.

300 MHz $^1$H-NMR DMSO-d$_6$): δ 9.52 (d, 1H); 8.10 (d, 1H); 7.86 (dd, 2H); 7.79 (ddd, 1H); 7.63 (m, 2H); 7.49-7.36 (m, 16H); 7.30-7.20 (m, 3H); 5.01 (dt, 1H); 4.09 (m, 4H); 3.99 (m, 2H); 3.00 (m, 2H); 1.81-1.71 (m, 2H); 0.82 (t, 3H);

MS (EI, TSQ 700, source °180 C., 70 V, 200 uA): 5.14; 223; 210; 132; 91.

TABLE 1

| Ex | Ar | R | $R_1$ | $R_2$ | * | Molecular formula | Melting point °C. | $[\alpha]_D^{20}$ c = 0.5, MeOH |
|---|---|---|---|---|---|---|---|---|
| 1 | Ph | Et | H | $OCH_2CO_2Et$ | (S) | $C_{29}H_{28}N_2O_4$ | 103–105 | –42.5 |
| 2 | Ph | Et | H | $OCH_2CO_2H$ | (S) | $C_{27}H_{24}N_2O_4 \cdot HCl$ | 203–204 | –30.2 |
| 3 | Ph | Et | H | $OCH_2CONH_2$ | (S) | $C_{27}H_{25}N_3O_3$ | 237–240 | –35.9 |
| 4 | Ph | Et | H | $OCH_2CONMe_2$ | (S) | $C_{29}H_{29}N_3O_3$ | 86–88 | –41.2 |
| 5 | Ph | Et | H | $OCO_2Et$ | (S) | $C_{28}H_{26}N_2O_4$ | 119–121 | –57.8[a] |
| 6 | Ph | Et | H | $NHCONHPh$ | (S) | $C_{32}H_{28}N_4O_2$ | 257–258 | –64.6[b] |
| 7 | Ph | Et | H | $NHCONHCH_2CO_2Et$ | (S) | $C_{30}H_{30}N_4O_4$ | 237–238 | –45.0[c] |
| 8 | Ph | Et | H | O-CH₂CH₂-NH-indanyl | (S) | $C_{36}H_{35}N_3O_2 \cdot HCl$ | 156–160 | –11.0 |
| 9 | Ph | Et | H | $OCH_2CH_2NHCOPh$ | (S) | $C_{34}H_{31}N_3O_3$ | 157–160 | –27.3 |
| 10 | Ph | Et | H | $OCH_2CH_2CH_2COOEt$ | (S) | $C_{31}H_{32}N_2O_4$ | 140–142 | –41.6[d] |
| 11 | Ph | Et | H | $OCH_2CH_2CH_2COOH$ | (S) | $C_{29}H_{28}N_2O_4$ | 149–151 | –42.3[d] |
| 12 | Ph | Et | H | $OCH_2CH_2NHCOCH_2Ph(o-CH_2OH)$ | (S) | $C_{36}H_{35}N_3O_4$ | 160–163 | –31.5 |
| 13 | Ph | Et | H | $(Z)\ OCH_2CH_2NHCOCH{=}CHCOOH$ | (S) | $C_{31}H_{29}N_3O_5$ | 158–162 | –38.6 |
| 14 | Ph | Et | H | $OCH_2CH_2NHCOCH_2CH_2COOH$ | (S) | $C_{31}H_{31}N_3O_5$ | 118–122 | –32.1 |
| 15 | Ph | Et | H | O-CH₂CH₂-NH-tropanyl(N-Me) | (S) | $C_{35}H_{40}N_4O_2 \cdot HCl$ | 200–203 | — |
| 16 | Ph | Et | H | $OCH_2CH_2NHCOPh(o-COOH)$ | (S) | $C_{35}H_{31}N_3O_5$ | 96–115 | –33.3 |
| 17 | Ph | Et | H | $OCH_2CH_2NHCOPh(o-COOMe)$ | (S) | $C_{36}H_{33}N_3O_5$ | 133–135 | –35.6 |
| 18 | Ph | Et | H | $(E)\ OCH_2CH_2NHCOCH{=}CHCOOMe$ | (S) | $C_{32}H_{31}N_3O_5$ | 122–125 | –37.7 |
| 19 | Ph | Et | H | $(Z)\ OCH_2CH_2NHCOCH{=}CHCOOMe$ | (S) | $C_{32}H_{31}N_3O_5$ | 80–90 | –37.2 |
| 20 | Ph | Et | H | $(E)\ OCH_2CH_2NHCOCH{=}CHCOOH$ | (S) | $C_{31}H_{29}N_3O_5$ | 230–233 | –39.6 |
| 21 | Ph | Et | H | $OCH_2C{\equiv}N$ | (S) | $C_{27}H_{23}N_3O_2$ | 70–72 | –40.4[d] |
| 22 | Ph | Et | H | $OCH_2CH_2NHCOCH_2Ph$ | (S) | $C_{35}H_{33}N_3O_3$ | 95–105 | –32.6 |
| 23 | Ph | Et | H | O-CH₂CH₂-NH-CO-CH(NH₂)-Ph (S-configured) | (S) | $C_{35}H_{34}N_4O_3$ | 140–145 | –17.0 |
| 24 | Ph | Et | H | O-CH₂CH₂-NH-CO-CH(NH₂)-Ph (R-configured) | (S) | $C_{35}H_{34}N_4O_3$ | 92–94 | –52.8 |
| 25 | Ph | Et | H | $OCH_2CH_2NHCOCH_2NH_2$ | (S) | $C_{29}H_{30}N_4O_3$ | 55–60 | –33.7 |
| 26 | Ph | Et | H | $OCH_2CH_2NHCOCH_2\text{-}(4\text{-pyridyl})$ | (S) | $C_{34}H_{32}N_4O_3$ | 76 dec. | –28.6 |
| 27 | Ph | Et | H | $OCH_2CH_2NHCOCH_2\text{-}(3\text{-pyridyl})$ | (S) | $C_{34}H_{32}N_4O_3$ | 89 dec. | –31.7 |
| 28 | Ph | Et | H | $OCH_2CH_2NHCOCH_2\text{-}(2\text{-pyridyl})$ | (S) | $C_{34}H_{32}N_4O_3$ | 74 dec. | –34.1 |
| 29 | Ph | Et | H | $OCH_2CH_2NHCOCH_2Ph(o-COOH)$ | (S) | $C_{36}H_{33}N_3O_5$ | 108 dec. | –28.3 |
| 30 | Ph | Et | H | $OCH_2CH_2NHCOPh(o-CH_2COOH)$ | (S) | $C_{36}H_{33}N_3O_5$ | 83 dec. | –33.5 |
| 31 | Ph | Et | H | $OCH_2CH_2NHCH_2Ph$ | (S) | $C_{34}H_{33}N_3O_2 \cdot HCl$ | 165–169 | –27.7 |
| 32 | Ph | Et | H | $OCH_2CH_2N(CH_2Ph)_2$ | (S) | $C_{41}H_{39}N_3O_2 \cdot HCl$ | 144–145 | –25.3 |

[a] C = 0.25, MeOH;
[b] C = 0.25, DMF;
[c] C = 0.1, DMF;
[d] C = 1, MeOH

TABLE 2

| Ex | Ar | R | $R_1$ | $R_2$ | * | Molecular formula | Molecular weight | Melting point ° C. | $[\alpha]_D^{20}$ c = 0.5, MeOH |
|---|---|---|---|---|---|---|---|---|---|
| 33 | Ph | Et | H | OCH$_2$CH$_2$NHCH$_2$CH$_2$Ph | (S) | C$_{35}$H$_{35}$N$_3$O$_2$.HCl | 529.680 | 113–115 | −10.4 |
| 34 | Ph | Et | H | OCH$_2$-(4-pyridyl) | (S) | C$_{31}$H$_{27}$N$_3$O$_2$ | 473.573 | 182–184 | −38.2 |
| 35 | Ph | Et | H | OCH$_2$CH$_2$NHCO-(3-carboxamidopyrazin-2-yl) | (S) | C$_{34}$H$_{32}$N$_6$O$_4$ | 588.665 | 121–123 | −30.9 |
| 36 | Ph | Et | H | OCH$_2$CH$_2$NHCO-(2-pyrazinyl) | (S) | C$_{32}$H$_{29}$N$_5$O$_3$ | 531.613 | 68–70 | −38.9 |
| 37 | Ph | Et | H | OCH$_2$CH$_2$NHCO-(3-aminopyrazin-2-yl) | (S) | C$_{32}$H$_{30}$N$_6$O$_3$ | 546.628 | 80–85 | −44.2 |
| 38 | Ph | Et | H | OCH$_2$CH$_2$CH$_2$NHCO-(2-pyrazinyl) | (S) | C$_{33}$H$_{31}$N$_5$O$_3$ | 545.640 | 70–75 | −31.6 |
| 39 | Ph | Et | H | OCH$_2$CH$_2$NHCOCH$_2$Ph(o—CH$_2$NHMe) | (S) | C$_{37}$H$_{38}$N$_4$O$_3$ | 586.732 | 58 dec. | 30.5 |
| 40 | Ph | Et | H | OCH$_2$CH$_2$NHCOCH$_2$Ph(o—CH$_2$pyrrolidino) | (S) | C$_{40}$H$_{42}$N$_4$O$_3$ | 626.797 | 89–95 | −34.2 |
| 41 | Ph | Et | H | OCH$_2$CH$_2$NHCOCH$_2$Ph(o—OCH$_2$CH$_2$pyrrolidino) | (S) | C$_{41}$H$_{44}$N$_4$O$_4$ | 656.823 | 132–134 | −30.1 |
| 42 | Ph | Et | H | OCH$_2$CH$_2$NHCOCH$_2$Ph(o—OH) | (S) | C$_{35}$H$_{33}$N$_3$O$_4$ | 559.663 | 160–161 | −34.7 |
| 43 | Ph | Et | H | OCH$_2$CH$_2$NHCOCH$_2$Ph(o—OMe) | (S) | C$_{36}$H$_{35}$N$_3$O$_4$ | 573.690 | 106–108 | −31.6 |

TABLE 3

Analytical and spectroscopic data of compounds of Examples 33–43.

| Ex. | Elemental analysis | IR (Kbr); cm$^{-1}$ | MS (EI; TSQ 700; source 180° C.; 70 eV; 200 μA) | 300 MHz $^1$H NMR (DMSO), 303 K |
|---|---|---|---|---|
| 33 | | 3388; 2930; 1630; 1563. | 438; 383; 320; 303; 291; 247; 219; 204; 119; 105; 91; 56. | 9.48 (d, 1H); 8.91 (s br, 1H); 8.09 (d, 1H); 7.98 (dd, 2H); 7.76 (ddd, 1H); 7.61 (m, 2H); 7.58–7.50 (m,3H); 7.48–7.25 (m, 8H); 7.21 (d, 2H); 5.07 (dt, 1H); 3.98–3.85 (m, 2H); 2.85 (s br, 6H); 1.90–1.74 (m, 2H); 0.93 (t, 3H). |
| 34 | | 3230; 3063–2868; 1626; 1586; 1541. | 473 (M+); 444; 381; 339; 312; 248; 220; 219; 190; 134; 91. | 9.37 (d, 1H); 8.41 (d, 2H); 8.11 (d, 1H); 7.94 (m, 2H): 7.79 (ddd, 1H); 7.70–7.60 (m, 2H); 7.50 (m, 3H); 7.40 (m, 2H); 7.30–7.20 (m, 3H); 6.98 (d, 2H); 5.07 (dt, 1H); 4.68 (s, 2H); 1.76 (dq, 2H); 0.90 (t, 3H). |
| 35 | Calcd. C, 69.37; H, 5.48; N, 14.28; Found C, 68.47; H, 5.50; N, 13.96. | 3280; 2965; 2877; 1700–1610. | 383; 247; 207; 190; 162; 91. | 9.28 (d, 1H); 8.73 (s, 2H); 8.25 (t, 1H); 8.05 (d, 1H); 7.95 (m, 3H); 7.71 (ddd, 1H); 7.60–7.37 (m, 10H); 7.28 (dd, 1H); 5.08 (dt, 1H); 3.70 (t, 2H); 3.05 (dt, 2H); 1.90–1.75 (m, 2H); 1.65–1.58 (m, 2H); 0.98 (t, 3H). |
| 36 | | 3276; 3062; 2969; 2879; 1690–1630; 1577. | 219; 150. | 9.30 (d, 1H); 9.11 (d, 1H); 8.88 (d, 1H); 8.70 (m, 1H); 8.60 (t, 1H); 8.04 (d, 1H); 7.92 (dd, 2H); 7.71 (ddd, 1H); 7.59 (m, 2H); 7.45–7.23 (m, 8H); 5.08 (dt, 1H); 3.89–3.78 (m, 2H); 3.41–3.25 (m, 2H); 1.89–1.72 (m, 2H); 0.92 (t, 3H). |
| 37 | | 3296; 3063; 2967; 2932; 2877; 1670; 1660; 1642; 1596. | 247; 219; 190; 165; 150; 119. | 9.29 (d, 1H); 8.41 (t, 1H); 8.21 (d, 1H); 8.03 (d, 1H); 7.92 (dd, 2H); 7.80 (d, 1H); 7.71 (ddd, 1H); 7.58 (m, 2H); 7.55–7.35 (m, 9H); 7.26 (dd, 1H); 5.08 (dt, 1H); 3.85–3.73 (m, 2H); 3.32–3.20 (m, 2H); 1.89–1.72 (m, 2H); 0.91 (t, 3H). |
| 38 | | 3393; 3289; 3060; 2965; 2932; 2876; 1680–1640; 1582. | 219; 164; 136. | 9.27 (d, 1H); 9.15 (d, 1H); 8.88 (d, 1H); 8.70 (m, 1H); 8.61 (t, 1H); 8.07 (d, 1H); 7.92 (d, 2H); 7.71 (ddd, 1H); 7.60–7.54 (m, 2H); 7.50–7.32 (m, 7H); 7.24 (dd, 1H); 5.08 (dt, 1H); 3.67 (t, 2H); 3.12 (dt, 2H); 1.89–1.72 (m, 2H); 1.68–1.59 (m, 2H); 0.98 (t, 3H). |
| 39 | | 3266; 2929; 1660–1650; 1541. | 586 (M+); 383; 264; 247; 219; 161; 119; 104; 91. | 9.29 (d, 1H); 8.33 (t, 1H); 8.08 (d, 1H); 7.97 (m, 2H); 7.72 (ddd, 1H); 7.59 (m, 2H); 7.51 (m, 3H); 7.43 (d, 2H); 7.36 (dd, 2H); 7.27 (m, 2H); 7.19–7.09 (m, 3H); 5.08 (dt, 1H); 3.60 (m, 4H); 3.40 (s, 2H); 3.10–2.90 (m, 2H); 2.21 (s, 3H); 1.81–1.75 (m, 2H); 0.96 (t, 3H). |
| 40 | | 3256; 3063; 2965; 2790; | 383; 264; 247; 219; 175; 119; 105; 91. | 9.28 (d, 1H); 8.24 (s br, 1H); 8.08 (d, 1H); 7.97 (m, 2H); 7.72 (ddd, 1H); 7.59 (m, 2H); 7.51 (m, 3H); 7.44 (d, 2H); |

TABLE 3-continued

Analytical and spectroscopic data of compounds of Examples 33–43.

| Ex. | Elemental analysis | IR (Kbr); cm$^{-1}$ | MS (EI; TSQ 700; source 180° C.; 70 eV; 200 μA) | 300 MHz $^1$H NMR (DMSO), 303 K |
|---|---|---|---|---|
|  |  | 1640; 1539. |  | 7.38 (dd, 2H); 7.30–7.10 (m, 5H); 5.08 (dt, 1H); 3.60 (m, 4H); 3.43 (s, 2H); 3.10–2.90 (m, 2H); 2.42 (m, 4H); 1.88–1.78 (m, 2H); 1.68–1.59 (m, 4H); 0.98 (t, 3H). |
| 41 | Calcd. C, 74.97; H, 6.75; N, 8.53; Found C, 72.86; H, 6.56; N, 8.21. | 3230; 3061; 2963; 2874; 1640–1630; 1601; 1536. | 559; 382; 177; 97; 84. | DMSO (+TFA): 9.67 (s br, 1H); 9.31 (d, 1H); 8.09 (d, 1H); 8.02 (t, 1H); 7.98 (m, 2H); 7.73 (dd, 1H); 7.60 (m, 2H); 7.51 (m, 3H); 7.44 (d, 2H); 7.39 (dd, 2H); 7.30–7.20 (m, 2H); 7.11 (d, 1H); 6.99 (d, 1H); 6.90 (dd, 1H); 5.08 (dt, 1H); 4.29 (t, 2H); 3.70–3.60 (m, 2H); 3.56–3.45 (m, 4H); 3.38 (s, 2H); 3.10–2.94 (m, 4H); 2.00–1.70 (m, 6H); 0.99 (t, 3H). |
| 42 | Calcd. C, 75.11; H, 5.94; N, 7.51; Found C, 75.07; H, 5.95; N, 7.43. | 3430; 3400–3100; 3061; 2964; 1660; 1632; 1520. | 559 (M+); 426; 408; 383; 264; 248; 178; 106; 100; 134; 91. | 9.60 (s br, 1H); 9.29 (d, 1H); 8.08 (d, 1H); 7.98 (dd, 2H); 7.80–7.70 (m, 2H); 7.59 (m, 2H); 7.51 (m, 3H); 7.44 (d, 2H); 7.38 (dd, 2H); 7.28 (dd, 1H); 7.02 (dd, 1H); 6.99 (d, 1H); 6.79 (d, 1H); 6.70 (dd, 1H); 5.09 (dt, 1H); 3.70–3.60 (m, 2H); 3.29 (s, 2H); 3.13–2.93 (m, 2H); 1.90–1.75 (m, 2H); 0.99 (t, 3H). |
| 43 | Calcd. C, 75.37; H, 6.15; N, 7.32; Found C, 75.43; H, 6.26; N, 7.19. | 3285; 3062; 2966; 2837; 1670–1630; 1603; 1587. | 573 (M+); 382; 264; 247; 220; 192; 160; 133; 91. | 9.30 (d, 1H); 8.08 (d, 1H); 7.99 (dd, 2H); 7.72 (ddd, 1H); 7.58 (m, 2H); 7.52 (m, 4H); 7.45 (d, 2H); 7.39 (dd, 2H); 7.29 (dd, 1H); 7.19 (dd, 1H); 7.02 (d, 1H); 6.91 (d, 1H); 6.83 (dd, 1H); 5.08 (dt, 1H); 3.70 (s, 3H); 3.70–3.55 (m, 2H); 3.28 (s, 2H); 3.03–2.94 (m, 2H); 1.90–1.75 (m, 2H); 0.98 (t, 3H). |

TABLE 4

Pharmacological data

| Example n. | Binding affinity in hNK-3-CHO$^a$ IC$_{50}$ (nM) |
|---|---|
| 2 | 1.9 |
| 8 | 1.3 |
| 9 | 2.2 |
| 11 | 1.7 |
| 14 | 2.3 |
| 22 | 0.6 |
| 25 | 2.6 |
| 26 | 0.9 |
| 29 | 0.8 |
| 30 | 1.5 |
| 34 | 1.6 |
| 36 | 0.2 |
| 38 | 0.4 |
| 40 | 1.3 |
| 42 | 0.4 |

$^a$hNK-3-CHO = human neurokinin-3 receptors expressed in CHO cell lines; radioligand used was [$^{125}$I]-[Me-Phe$^7$]-NKB.

What is claimed is:

1. A compound of formula (I):

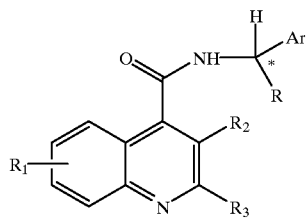

(I)

or a solvate thereof, or a salt thereof, wherein, Ar is an optionally substituted aryl or a $C_{5-7}$ cycloalkdienyl group, or an optionally substituted single or fused ring aromatic heterocyclic group;

R is $C_{1-6}$ alkyl, $C_{3-7}$ cycloalkyl, $C_{3-7}$ cycloalkylalkyl, optionally substituted phenyl or phenyl $C_{1-6}$ alkyl, an optionally substituted five-membered heteroaromatic ring comprising up to four heteroatoms selected from O and N, hydroxy $C_{1-6}$ alkyl, amino $C_{1-6}$ alkyl, $C_{1-6}$ alkylaminoalkyl, di $C_{1-6}$ alkylaminoalkyl, $C_{1-6}$ acylaminoalkyl, $C_{1-6}$ alkoxyalkyl, $C_{1-6}$ alkylcarbonyl, carboxy, $C_{1-6}$ alkoxyxcarbonyl, $C_{1-6}$ alkoxycarbonyl $C_{1-6}$ alkyl, aminocarbonyl, $C_{1-6}$ alkylaminocarbonyl, di $C_{1-6}$ alkylaminocarbonyl, halogeno $C_{1-6}$ alkyl; or R is a group —(CH$_2$)$_p$— wherein p is 2 or 3 which group forms a ring with a carbon atom of Ar;

R$_1$ represents hydrogen or up to four optional substituents selected from the list consisting of: $C_{1-6}$ alkyl, $C_{1-6}$ alkenyl, aryl, $C_{1-6}$ alkoxy, hydroxy, halogen, nitro, cyano, carboxy, carboxamido, sulphonamido, $C_{1-6}$ alkoxycarbonyl, trifluoromethyl, acyloxy, phthalimido, amino or mono- and di-$C_{1-6}$ alkylamino; R$_2$ represents a moiety —O—(CH$_2$)$_n$—X wherein X is carboxy, $C_{1-6}$ alkoxycarbonyl, aminocarbonyl, mono- or di-$C_{1-6}$ alkylaminocarbonyl; or X is a group —NX$_1$X$_2$ wherein X$_1$ and X$_2$ each independently represent hydrogen, carboxyalkylcarbonyl, alkoxycarbonylalkylcarbonyl, alkylcarbonyl, arylcarbonyl, heteroarylcarbonyl, aryl-$C_{1-6}$-alkylcarbonyl, heteroaryl $C_{1-6}$-alkylcarbonyl, aminocarbonyl, mono- or bis-$C_{1-6}$ alkylaminocarbonyl, amino $C_{1-6}$ alkylcarbonyl, mono- or bis-$C_{1-6}$ alkylamino $C_{1-6}$ alkylcarbonyl, a moiety of formula —CO—T—CO—T$_1$ or a 5 to 9 membered single or fused ring cycloalkyl group optionally comprising 1 or 2 nitrogen atoms and optionally 1 or 2 additional heteroatoms selected from O or N and wherein one or two ring atoms are optionally substituted with $C_{1-6}$ alkyl, said ring being optionally fused to a benzene ring; wherein the above mentioned aryl and herteroaryl groups are optionally substituted with up to two groups selected from hydroxy, $C_{1-6}$ alkoxy, hydroxy-$C_{1-6}$ alkyl, amino-$C_{1-6}$-alkyl, mono- or bis- $C_{1-6}$-alkylamino, mono- bis-$C_{1-6}$-alkylamino-$C_{1-6}$- alkyl, amino-$C_{1-6}$-alkoxy, mono- or bis- $C_{1-6}$-alkylamino-$C_{1-6}$-alkoxy, carboxy, C-$_{1-6}$-alkylcarbonyl, C-$_{1-6}$-alkoxycarbonyl, carboxy-$C_{1-6}$ alkyl, carboxy-$C_{1-6}$ alkoxy and C-$_{1-6}$-alkylcarbonyl $C_{1-6}$ alkoxy; and wherein the alkyl moiety of any heteroaryl-$C_{1-6}$-alkyl or aryl-$C_{1-6}$-alkyl group is optionally substituted with an amino, a mono-$C_{1-6}$-alkylamino or a bis-$C_{1-6}$-alkyl amino group; or X is a C-linked single or fused ring heterocyclic group, any ring being saturated or unsaturated and consisting of 5- to 6-ring atoms, said ring atoms comprising 1 or 2 nitrogen atoms and optionally 1 or 21 additional heteroatoms selected from O or N and wherein one or two ring atoms are optionally substituted with $C_{1-6}$ alkyl, hydroxy, amino, mono- or bis-$C_{1-6}$-alkylamino or an oxo substituent; and n is zero or an integer in the range of from 1 to 7 providing that when X is a group —$NX_1X_2$, n is only an integer in the range of from 2 to 7 and providing that $X_1$ and $X_2$ are not simultaneously hydrogen; or $R_2$ represents a moiety-NH—CO—NHY wherein Y represents $C_{1-6}$-alkyl, aryl, aryl $C_{1-3}$-alkyl, a moiety —$(CH_2)_p$—$X_3$ wherein p is an integer in the range of from 1 to 4 and $X_3$ is carboxy, $C_{1-6}$ alkoxycarbonyl, or a moiety —CO—NH—$(CH_2)_q$—$NX_4X_5$ wherein q is an integer in the range of from 2 to 4 and $X_4$ and $X_5$ each independently represent hydrogen, $C_{1-6}$ alkyl or $C_{1-6}$ alkylcarbonyl;

$R_3$ is branched or linear $C_{1-6}$ alkyl, $C_{3-7}$ cycloalkyl, $C_{4-7}$ cycloalkylalkyl, optionally substituted aryl, or an optionally substituted single or fused ring aromatic heterocyclic group;

T is a $C_{1-6}$ alkylene or $C_{2-6}$ alkenylene group; and $T_1$ is hydroxy or $C_{1-6}$ alkoxy.

2. The compound according to claim 1, wherein Ar represents phenyl.

3. The compound according to claim 1, wherein R represents ethyl.

4. The compound according to claim 1, wherein $R_1$ represents hydrogen.

5. The compound according to claim 1, wherein $R_2$ is a group —O—$(CH_2)_n$—X wherein X represents carboxy or $C_{1-6}$ alkoxycarbonyl or a C-linked single or fused ring heterocyclic group as defined in relation to formula (I).

6. The compound according to claim 1, wherein $R_2$ is —O—$(CH_2)_n$—X wherein n is an integer 2 or 3 and X is a group —$NX_1X_2$ wherein $X_1$ is hydrogen and $X_2$ is a moiety of the above defined formula —CO—T—CO—$T_1$, substituted aryl-$C_{1-6}$-alkylcarbonyl or heteroarylcarbonyl.

7. The compound according to claim 1, wherein Ar is phenyl, R is ethyl, $R_1$ is hydrogen and $R_2$ is a moiety —O—$(CH_2)_n$—X wherein either:

n is 1, 2 or 3 and X is carboxy, $C_{1-6}$ alkoxycarbonyl, for example ethoxycarbonyl, or the C-linked single or fused ring heterocyclic group defined in relation to formula (I), for example pyridyl; or n is 2 or 3 and X is a group —$NX_1X_2$ wherein $X_1$ is hydrogen and $X_2$ is moiety of the above defined formula —CO—T—CO—$T_1$, for example wherein T is ethylene and $T_1$ is OH, or $X_2$ is substituted aryl-$C_{1-6}$-alkylcarbonyl, for example (2-carboxy)benzylcarbonyl and (2-pyrrolidinomethyl)benzylcarbonyl or heteroarylcarbonyl, for example 2-pyrazinylcarbonyl.

8. The compound according to claim 1, selected from Examples 1–43 herein, or a salt thereof, or a solvate thereof.

9. The compound according to claim 1, selected from Examples 1, 2, 11, 14, 29, 34, 38, 39 and 40, or a salt thereof, or a solvate thereof.

10. A pharmaceutical composition comprising a compound of formula (I), according to claim 1, or a pharmaceutically acceptable salt thereof, or pharmaceutically acceptable solvate thereof and a pharmaceutically acceptable carrier.

11. A method for the treatment and/or prophylaxis of respiratory diseases; inflammatory diseases; neurogenic inflammation or peripheral neuropathy, allergies; ophthalmic diseases; cutaneous diseases, skin disorders and itch; adverse immunological reactions and disorders related to immune enhancement or suppression; gastrointestinal (GI) disorders and diseases of the GI tract; renal disorders and disorders of the bladder function, disorders of the central nervous system; neurodegenerative disorders of the Alzheimer type, Alzheimer's disease, Down's syndrome, Huntington's; demyelinating diseases and other neuropathological disorders; addiction disorders; stress related somatic disorders; reflex sympathetic dystrophy; dysthymic disorders; eating disorders; fibrosing and collagen diseases; disorders of the blood flow caused by vasodilation and vasospastic diseases and pain or nociception that is attributable to or associated with any of the foregoing conditions which method comprises administering to a mammal in need of such treatment and/or prophylaxis an effective, non-toxic amount of a compound of formula (I), according to claim 1, or a pharmaceutically acceptable salt thereof, or a pharmaceutically acceptable solvate thereof.

12. A process for the preparation of a compound of formula (I), according to claim 1, or a salt thereof and/or a solvate thereof, which process comprises reacting a compound of formula (III):

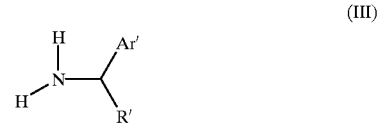

(III)

wherein R' and Ar' are R and Ar as defined for formula (I) or a group or atom convertible to R and Ar respectively, with a compound of formula (II) or an active derivative thereof:

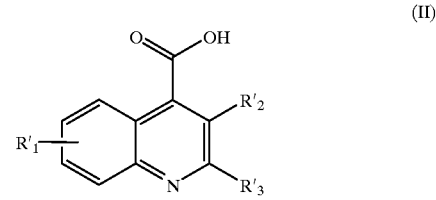

(II)

wherein $R'_1$, $R'_2$ and $R'_3$ are $R_1$, $R_2$ and $R_3$ respectively as defined in relation to formula (I) or a group convertible to $R_1$, $R_2$ and $R_3$ to form a compound of formula (Ib):

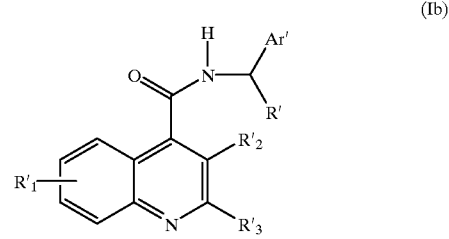

(Ib)

wherein Ar', R', $R'_1$, $R'_2$ and $R'_3$ are as defined above, and optionally thereafter carrying out one or more of the following optional steps:
(i) converting any one of Ar', R', $R'_1$, $R'_2$ and $R'_3$ to Ar, R, $R_1$, $R_2$ or $R_3$ respectively as required, to obtain a compound of formula (I);

(ii) converting a compound of formula (I) into another compound formula (I); and (iii) preparing a salt of the compound of formula (I) and/or a solvate thereof.

13. The method of claim 11, wherein the respiratory diseases are selected from chronic obstructive pulmonary disease (COPD), asthma, airway hyperreactivity, and cough.

14. The method of claim 11, wherein the inflammatory diseases are selected from inflammatory bowel disease, psoriasis, fibrositis, osteoarthritis, rheumatoid arthritis and inflammatory pain.

15. The method of claim 11, wherein the allergies are selected from eczema and rhinitis.

16. The method of claim 11, wherein the ophthalmic diseases are selected from ocular inflammation, conjunctivitis, and vernal conjuctivitis.

17. The method of claim 11, wherein the cutaneous diseases are selected from cutaneous wheal and flare, contact dermatitis, atopic dermatitis, urticaria and other eczematoid dermatitis.

18. The method of claim 11, wherein the adverse immunological reaction is rejection of transplanted tissues.

19. The method of claim 11, wherein the disorder related to immune enhancement or suppression is systemic lupus erythematosis.

20. The method of claim 11, wherein the GI disorders and diseases of the GI tract are selected from disorders associated with the neuronal control of viscera.

21. The method of claim 20, wherein the disorders associated with the neuronal control of viscera are selected from ulcerative colitis, Crohn's disease and urinary incontinence.

22. The method of claim 11, wherein the disorders of the central nervous system are selected from anxiety, depression, psychosis and schizophrenia.

23. The method of claim 11, wherein the neurodegenerative disorders are selected from AIDS related dementia, senile dementia of the Alzheimer type, Alzheimer's disease, Down's syndrome, Huntington's disease, Parkinson's disease, movement disorders and convulsive disorders.

24. The method of claim 11, wherein the demyelinating diseases are selected from multiple sclerosis and amyotrophic lateral sclerosis.

25. The method of claim 11, wherein the neuropathological disorders are selected from diabetic neuropathy, AIDS related neuropathy, chemotherapy-induced neuropathy and neuralgia.

26. The method of claim 11, wherein the addiction disorder is alcoholism.

27. The method of claim 11, wherein the disorders of the blood flow caused by vasodilation and vasospastic diseases are selected from angina, migraine and Reynaud's disease.

28. The method of claim 11, wherein the fibrosing and collagen diseases are selected from scleroderma and eosinophilic fascioliasis.

29. The method of claim 11, wherein the pain or nociception is the transmission of pain in migraine.

* * * * *